(12) United States Patent
Budelli et al.

(10) Patent No.: US 11,771,102 B2
(45) Date of Patent: *Oct. 3, 2023

(54) PROBIOTIC COMPOSITIONS AND METHODS

(71) Applicant: H.J. Heinz Company Brands LLC, Pittsburgh, PA (US)

(72) Inventors: Andrea Budelli, Gallarate (IT); Francesca Romana Fasano, Sondrio (IT); Miryam Terzano, Milan (IT); Lorenzo Bramati, Monza (IT)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 144 days.

This patent is subject to a terminal disclaimer.

(21) Appl. No.: 17/223,456

(22) Filed: Apr. 6, 2021

(65) Prior Publication Data
US 2021/0259264 A1 Aug. 26, 2021

Related U.S. Application Data

(60) Division of application No. 16/360,154, filed on Mar. 21, 2019, now Pat. No. 11,109,603, which is a
(Continued)

(51) Int. Cl.
*A23C 9/123* (2006.01)
*A23L 7/104* (2016.01)
(Continued)

(52) U.S. Cl.
CPC ............ *A23C 9/1234* (2013.01); *A23C 9/127* (2013.01); *A23L 7/10* (2016.08); *A23L 7/104* (2016.08);
(Continued)

(58) Field of Classification Search
None
See application file for complete search history.

(56) References Cited

U.S. PATENT DOCUMENTS 5,968,569 A 10/1999 Cavadini
6,599,504 B1 7/2003 Wadstrom
(Continued)

FOREIGN PATENT DOCUMENTS

CA 2761691 11/2010
CN 1350461 5/2002
(Continued)

OTHER PUBLICATIONS

Adams, Clifford A. "The Probiotic Paradox: Live and Dead Cells Are Biological Response Modifiers." Nutrition Research Reviews, 2010, vol. 23, No. 1, pp. 37-46.
(Continued)

*Primary Examiner* — David W Berke-Schlessel
(74) *Attorney, Agent, or Firm* — Fitch, Even, Tabin & Flannery LLP

(57) ABSTRACT

The present invention features compositions and methods for modulation of the mucosal immune system. The compositions include foods fermented by the probiotic organism, *Lactobacillus paracasei* CBA L74 (International Depository Accession Number LMG P-24778). Alternatively the compositions can include *L. paracasei* CBA L74 and a physiologically acceptable carrier. In some embodiments, the *L. paracasei* CBA L74 can be non-replicating. The compositions can be administered to a subject having or at risk for gastrointestinal disorders related to immaturity of the immune system, infection or disease.

11 Claims, 39 Drawing Sheets

Related U.S. Application Data continuation of application No. 15/393,904, filed on Dec. 29, 2016, now Pat. No. 10,251,407, which is a division of application No. 14/127,573, filed as application No. PCT/US2012/042959 on Jun. 18, 2012, now Pat. No. 10,039,296.

(60) Provisional application No. 61/498,910, filed on Jun. 20, 2011.

(51) Int. Cl.

| | | |
|---|---|---|
| *A23L 7/10* | (2016.01) | |
| *A23L 19/00* | (2016.01) | |
| *A23L 33/135* | (2016.01) | |
| *A61K 35/747* | (2015.01) | |
| *A23C 9/127* | (2006.01) | |
| *A23L 33/00* | (2016.01) | |
| *A61K 35/00* | (2006.01) | |

(52) U.S. Cl.
CPC ............. *A23L 19/00* (2016.08); *A23L 33/135* (2016.08); *A23L 33/40* (2016.08); *A61K 35/747* (2013.01); *A23V 2002/00* (2013.01); *A23Y 2220/63* (2013.01); *A61K 2035/115* (2013.01)

(56) References Cited

U.S. PATENT DOCUMENTS

| | | | |
|---|---|---|---|
| 6,835,376 | B1 | 12/2004 | Neeser |
| 9,980,991 | B2 | 5/2018 | Fasano |
| 10,039,296 | B2 | 8/2018 | Budelli |
| 10,245,300 | B2 | 4/2019 | Fasano |
| 10,251,407 | B2 | 4/2019 | Budelli |
| 10,258,656 | B2 | 4/2019 | Fasano |
| 2004/0005305 | A1 | 1/2004 | Spivey-Krobath |
| 2006/0018890 | A1 | 1/2006 | Isolauri |
| 2006/0233772 | A1 | 10/2006 | Herz |
| 2007/0042021 | A1 | 2/2007 | Schiffrin |
| 2007/0207132 | A1 | 9/2007 | Speelmans |
| 2007/0274983 | A1 | 11/2007 | Kluijtmans |
| 2008/0199446 | A1 | 8/2008 | Vriesema |
| 2009/0004164 | A1 | 1/2009 | Speelmans |
| 2009/0136643 | A1 | 5/2009 | Bovetto |
| 2009/0186142 | A1 | 7/2009 | Tatewaki et al. |
| 2009/0203592 | A1 | 8/2009 | Beermann |
| 2009/0304655 | A1 | 12/2009 | Donnet-Hughes |
| 2010/0196341 | A1 | 8/2010 | Wei |
| 2010/0278781 | A1 | 11/2010 | Hougee |
| 2011/0028434 | A1 | 2/2011 | Destaillats |
| 2011/0064707 | A1 | 3/2011 | Rochat |
| 2011/0070334 | A1 | 3/2011 | Rangavajla |
| 2011/0293724 | A1 | 12/2011 | Hausch |
| 2011/0293784 | A1 | 12/2011 | Wittke |
| 2012/0014963 | A1 | 1/2012 | Benyacoub |
| 2013/0129860 | A1 | 5/2013 | Chavez |
| 2014/0377238 | A1 | 12/2014 | Budelli |
| 2015/0174199 | A1 | 6/2015 | Fasano |
| 2016/0113973 | A1 | 4/2016 | Fasano |
| 2017/0065648 | A1 | 3/2017 | Fasano |
| 2017/0202231 | A1 | 7/2017 | Budelli |
| 2018/0271920 | A1 | 9/2018 | Fasano |
| 2019/0281846 | A1 | 9/2019 | Budelli |

FOREIGN PATENT DOCUMENTS

| | | |
|---|---|---|
| CN | 101451158 | 6/2009 |
| CN | 102021127 | 4/2011 |
| CN | 102046028 | 5/2011 |
| CN | 102065872 | 5/2011 |
| EP | 0130228 | 1/1985 |
| EP | 1364586 | 11/2003 |
| EP | 1723951 | 11/2006 |
| EP | 1972207 | 9/2008 |
| EP | 2452572 | 5/2012 |
| EP | 2452574 | 5/2012 |
| EP | 1565547 | 9/2012 |
| EP | 2510932 | 10/2012 |
| EP | 2648551 | 10/2013 |
| RU | 2134583 | 8/1999 |
| RU | 2205871 | 6/2003 |
| RU | 2243779 | 1/2005 |
| RU | 2385730 | 7/2008 |
| SE | 522747 | 3/2004 |
| WO | 9716079 | 5/1997 |
| WO | 1997049303 | 12/1997 |
| WO | 9902170 | 1/1999 |
| WO | 1999029833 | 6/1999 |
| WO | 9951114 | 10/1999 |
| WO | 0053201 | 9/2000 |
| WO | 0160346 | 8/2001 |
| WO | 2001097822 | 12/2001 |
| WO | 2002018542 | 3/2002 |
| WO | 0228402 | 4/2002 |
| WO | 2002053706 | 7/2002 |
| WO | 03070203 | 8/2003 |
| WO | 2004112509 | 12/2004 |
| WO | 2007093619 | 8/2007 |
| WO | 2007101675 | 9/2007 |
| WO | 2007140622 | 12/2007 |
| WO | 2008003782 | 1/2008 |
| WO | 2008006849 | 1/2008 |
| WO | 2008017455 | 2/2008 |
| WO | 2008055651 | 5/2008 |
| WO | 2008071667 | 6/2008 |
| WO | 2008116700 | 10/2008 |
| WO | 2008116708 | 10/2008 |
| WO | 2008116892 | 10/2008 |
| WO | 2008116904 | 10/2008 |
| WO | 2008116907 | 10/2008 |
| WO | 2008116916 | 10/2008 |
| WO | 2009030452 | 3/2009 |
| WO | 2009030488 | 3/2009 |
| WO | 2009034162 | 3/2009 |
| WO | 2009034165 | 3/2009 |
| WO | 2009059996 | 5/2009 |
| WO | 2009060073 | 5/2009 |
| WO | 2009067000 | 5/2009 |
| WO | 2009068549 | 6/2009 |
| WO | 2009077352 | 6/2009 |
| WO | 2009092628 | 7/2009 |
| WO | 2009106528 | 9/2009 |
| WO | 2009112361 | 9/2009 |
| WO | 2009138680 | 11/2009 |
| WO | 2009144137 | 12/2009 |
| WO | 2009151315 | 12/2009 |
| WO | 2009156307 | 12/2009 |
| WO | 2010002244 | 1/2010 |
| WO | 2010003790 | 1/2010 |
| WO | 2010003803 | 1/2010 |
| WO | 2010003878 | 1/2010 |
| WO | 2010008272 | 1/2010 |
| WO | 2010010021 | 1/2010 |
| WO | 2010033424 | 3/2010 |
| WO | 2010034624 | 4/2010 |
| WO | 2010048481 | 4/2010 |
| WO | 2010060722 | 6/2010 |
| WO | 2010066569 | 6/2010 |
| WO | 2010069737 | 6/2010 |
| WO | 2010081604 | 7/2010 |
| WO | 2010112430 | 10/2010 |
| WO | 2010130641 | 11/2010 |
| WO | 2010130643 | 11/2010 |
| WO | 2010130661 | 11/2010 |
| WO | 2010130702 | 11/2010 |
| WO | 2010143940 | 12/2010 |
| WO | 2011020748 | 2/2011 |
| WO | 2011039328 | 4/2011 |
| WO | 2011060123 | 5/2011 |
| WO | 2011110884 | 9/2011 |
| WO | 2011121379 | 10/2011 |
| WO | 2011148221 | 12/2011 |

(56) References Cited

FOREIGN PATENT DOCUMENTS

| WO | 2011149335 | 12/2011 |
|---|---|---|
| WO | 2012042013 | 4/2012 |
| WO | 2012059501 | 5/2012 |
| WO | 2012059502 | 5/2012 |
| WO | 2012062781 | 5/2012 |
| WO | 2012065810 | 5/2012 |
| WO | 2012069415 | 5/2012 |
| WO | 2012069416 | 5/2012 |
| WO | 2012076052 | 6/2012 |
| WO | 2012076321 | 6/2012 |
| WO | 2012076322 | 6/2012 |
| WO | 2012080205 | 6/2012 |
| WO | 2012107865 | 8/2012 |
| WO | 2012135126 | 10/2012 |
| WO | 2012140031 | 10/2012 |
| WO | 2012143362 | 10/2012 |
| WO | 2012156273 | 11/2012 |
| WO | 2012177556 | 12/2012 |
| WO | 2014183050 | 11/2014 |

OTHER PUBLICATIONS

Agostoni, Carlo, et al., "Fermented Infant Formulae Without Live Bacteria." Journal of Pediatric Gastroenterology and Nutrition, 2007, vol. 44, pp. 392-397.

Bar, F., et al., "Cell-free Supernatants of *Escherichia coli* Nissle 1917 Modulate Human Colonic Motility: Evidence from an in Vitro Organ Bath Study." Neurogastroenterol Motil, 2009, vol. 21, pp. 559-566.

Campeotto, Florence, et al., "A Fermented Formula in Pre-Term Infants: Clinical Tolerance, Gut Microbiota, Down-Regulation of Faecal Calprotectin and Up-Regulation of Faecal Secretory IgA." British Journal of Nutrition, 2011, vol. 105, pp. 1843-1851.

Chapat, Ludivine, et al., "Lactobacillus casei Reduces CD8+ T Cell-Mediated Skin Inflammation." European Journal of Immunology, 2004, vol. 34, pp. 2520-2528.

Chiang, Shen-Shih, et al., "Beneficial Effects of Lactobacillus paracasei subsp. paracasei NTU 101 and Its Fermented Products." Applied Microbiology Biotechnology, 2012, vol. 93, pp. 903-916.

Chinese Office Action, Chinese Application No. 201480026882.7, dated Aug. 9, 2018, 19 pages (with English translation).

Chinese Patent Application No. 201280040658.4, First Office Action dated Mar. 11, 2015, 6 pages.

Chinese Patent Application No. 201280040658.4, Second Office Action dated Aug. 24, 2015, 3 pages.

Chinese Patent Application No. 201380032073.2, First Office Action dated Jan. 25, 2016, 15 pages (with English translation).

D'Arienzo, R., et al., "Distinct Immunomodulatory Properties of Lactobacillus Paracasei Strains." Journal of Applied Microbiology, 2011, vol. 111, pp. 1482-1491.

D'Arienzo, Rossana, et al., "Modulation of the Immune Response by Probiotic Strains in a Mouse Model of Gluten Sensitivity." Cytokine, 2009, vol. 48, pp. 254-259.

De Angelis, Maria, et al., "VSL#3 Probiotic Preparation Has the Capacity to Hydrolyze Gliadin Polypeptides Responsible for Celiac Sprue." Biochimica et Biophysica Acta, 2006, vol. 1762, No. 1, 2006, pp. 80-93.

Di Cagno, Raffaella, et al., "Sourdough Bread Made from Wheat and Nontoxic Flours and Started with Selected Lactobacilli Is Tolerated in Celiac Sprue Patients." Applied and Environmental Microbiology, Feb. 2004, vol. 70, No. 2, pp. 1088-1096.

Di Cagno, Raffaella, et al., "Use of Selected Sourdough Strains of Lactobacillus for Removing Gluten and Enhancing the Nutritional Properties of Gluten-Free Bread." Journal of Food Protection, vol. 71, No. 7, 2008, pp. 1491-1495.

Dong, Honglin, et al., "Comparative Effects of Six Probiotic Strains on Immune Function in vitro." British Journal of Nutrition, 2012, vol. 108, pp. 459-470.

Elias, Peter M., ""Outside-to-Inside" (and Now Back to "Outside") Pathogenic Mechanisms in Atopic Dermatitis." Journal of Investigative Dermatology, May 2008, vol. 128, No. 5, pp. 1067-1070.

European Extended Search Report, European Application No. 14795405. 1, dated Oct. 17, 2016, 7 pages.

European Patent Application No. 12803279, Supplemental European Search Report, dated Apr. 7, 2015, 11 pages.

European Patent Application No. 13807318, Supplemental European Search Report, dated Dec. 11, 2015, 7 pages.

Examination Report for European Patent Application No. 18166007.7 dated Apr. 29, 2021.

Gallo, Marianna. "Formulation of Functional Food Using Constituents Modified by Biochemical and Physical Processes," PhD Dissertation, Universita degil studi di Napoli, Department of Engineering Chemistry, 2009, pp. 1-132.

Gardiner, Gillian E., et al., "A Spray-Dried Culture for Probiotic Cheddar Cheese Manufacture." International Dairy Journal, vol. 12, 2002, pp. 749-756.

Grandy, Giuseppe, et al., "Probiotics in the Treatment of Acute Rotavirus Diarrohoea. A Randomized, Double-Blind, Controlled Trial Using Two Different Probiotic Preparations in Bolivian Children." BMC Infectious Diseases, 2010, vol. 10, pp. 1-7.

Indrio, Flavia, et al., "Effect of a Fermented Formula on Thymus Size and Stool pH in Healthy Term Infants." Pediatric Research, 2007, vol. 62, No. 1, pp. 98-100.

International Patent Application No. PCT/US2012/042959, International Preliminary Report on Patentability and Written Opinion, dated Dec. 23, 2013, 8 pages.

International Patent Application No. PCT/US2012/042959, International Search Report, dated Feb. 1, 2013, 6 pages.

International Patent Application No. PCT/US2013/046286, International Preliminary Report on Patentability and Written Opinion, dated Dec. 23, 2014, 7 pages.

International Patent Application No. PCT/US2013/046286, International Search Report, dated Aug. 23, 2013, 5 pages.

International Patent Application No. PCT/US2014/037517, International Preliminary Report on Patentability and Written Opinion, dated Nov. 10, 2015, 5 pages.

International Patent Application No. PCT/US2014/037517, International Search Report, dated Sep. 11, 2014, 3 pages.

Iversen, Carol, et al., "*Cronobacterger* nov., a new genus to accommodate the biogroups of Enterobacter sakazakii, and proposal of *Cronobacter sakazakii* gen. nov., Cronobacter malonaticus . . . " International Journal of Systematic and Evolutionary Microbiology, 2008, vol. 58, pp. 1442-1447.

Jimenez, Esther, et al., "Is meconium from healthy newborns actually sterile?" Research in Microbiology, vol. 159, 2008, pp. 187-193.

Kalliomaki, Marko, et al., "Distinct Pattens of Neonatal Gut Microflora in Infants in Whom Atopy Was and Was Not Developing." Journal of Allergy and Clinical Immunology, Jan. 2001, vol. 107, No. 1, pp. 129-134.

Kearney, N., et al., "Development of a Spray Dried Probiotic Yoghurt Containing Lactobacillus Paracasei NFBC 338." International Dairy Journal, 2009, vol. 19, pp. 684-689.

Kirjavainen, P.V., et al., "Aberrant Composition of Gut Microbiota of Allergic Infants: A Target of Bifidobacterial Therapy at Weaning?" Gut, 2002, vol. 51, pp. 51-55.

Kristo, E., et al., "Modelling of Rheological, Microbiological and Acidification Properties of a Fermented Milk Products Containing a Probiotic Strain of Lactobacillus Paracasei." International Dairy Journal, vol. 13, 2003, pp. 517-528.

Lee, Joohee, et al., "Meta-Analysis of Clinical Trials of Probiotics for Prevention and Treatment of Pediatric Atopic Dermatitis." Journal of Allergy and Clinical Immunology, Jan. 2008, vol. 121, No. 1, pp. 116-121.

M'hir, Sana, et al., "Gluten Proteolysis as Alternative Therapy for Celiac Patients: A Mini-Review." African Journal of Biotechnology, Apr. 10, 2012, vo. 11, No. 29, pp. 7323-7330.

Martín-Diana, A.B., et al., "Development of a Fermented Goat's Milk Containing Probiotic Bacteria." International Dairy Journal, 2003, vol. 13, issue 10, pp. 827-833, Abstract only.

(56) References Cited

OTHER PUBLICATIONS

Moroi, Miki, et al., "Beneficial Effect of a Diet Containing Heat-Killed Lactobacillus Paracasei K71 on Adult Type Atopic Dermatitis." Journal of Dermatology, 2011, vol. 38, pp. 131-139.

Ortiz-Andrellucchi, Adriana, et al., "Immunomodulatory Effects of the Intake of Fermented Milk with Lactobacillus casei DN114001 in Lactating Mothers and Their Children." British Journal of Nutrition, 2008, vol. 100, pp. 834-845.

Rizzello, Carlo G. et al., "Highly Efficient Gluten Degradation by Lactobacilli and Fungal Proteases during Food Processing: New Perspectives for Celiac Disease." Applied and Environmental Microbiology, Jul. 2007, vol. 73, No. 14, pp. 4499-4507.

Robert, Herve, et al., "Biodiversity of lactic bacteria in French wheat sourdough as determined by molecular characterization using species-specific PCR." International Journal of Food Microbiology, 2009, vol. 135, No. 1, pp. 53-59.

Russian Office Action, Russian Patent Application No. 2015150082, dated Mar. 5, 2018, 16 pages (with English translation).

Russian Patent Application No. 2014101392/20, Office Action dated Aug. 4, 2014, 3 pages.

Sanz, Yolanda, et al., "Unraveling the Ties Between Celiac Disease And Intestinal Microbiota." International Reviews of Immunology, 2011, vol. 30, pp. 207-218.

Satoh, Yayoi, et al., "Bifidobacteria Prevents Necrotizing Enterocolitis and Infection in Preterm Infants." International Journal of Probiotics and Prebiotics, 2007, vol. 2, No. 2/3, pp. 149-154.

Savijoki, Kirsi, et al. "Purification and Molecular Characterization of a Tripeptidase (PepT) from Lactobacillus helveticus." Applied and Environmental Microbiology, Feb. 2000, vol. 66, No. 2, pp. 794-800.

Wagner, R. Doug, et al., "Probiotic Effects of Feeding Heat-Killed Lactobacillus acidophilus and Lactobacillus casei to Candida albicans-Colonized Immunodeficient Mice." Journal of Food Protection, 2000, vol. 63, No. 5, pp. 638-644, Abstract only.

Wang, N.-F., et al., "Evaluation of Peanut Flour Fermented with Lactic Acid Bacteria as a Probiotic Food." Food Science and Technology International, 2007, vol. 13, No. 6, pp. 469-475.

Winkler, Petra, et al., "Molecular and Cellular Basis of Microflora-Host Interactions." The Journal of Nutrition, 2007, vol. 137, pp. 756S-772S.

Zhou, Xiaodan, et al., "Laxative Effect of Lactobacillus paracasei LC-01 on Constipation Mice." Science and Technology of Dairy Industry. 2012, vol. 35, No. 5, pp. 7-11.

European Examination Report for EP 18166007.7, dated Jun. 7, 2023, 5 pages.

|  | CD 80 | CD 86 | CD40 | MHCII |
|---|---|---|---|---|
| CONTROL CaCo2 | 70.84±6.5 | 81.77±6.7 | 69.97±5.1 | 61.69±6.4 |
| CaCo2 + L. paracasei CBA-L74 ALIVE | 49.01±4.9* | 68.51±4.4 | 58.13±6.4 | 56.27±1.8 |
| CaCo2 + L. paracasei CBA-L74 INACTIVATED | 54.09±3.5 | 68.34±2.5 | 57.96±2.3 | 61.55±2.4 |
| CONTROL CACO2 + LPS | 76.51±2.9 | 87.56±2.99 | 73.01±2.2 | 71.93±2.4 |
| CaCo2 + L. paracasei CBA-L74 ALIVE + LPS | 49.32±1.7° | 58.09±3.3° | 59.34±4.1 | 52.75±2.1° |
| CaCo2 + L. paracasei CBA-L74 INACTIVATED + LPS | 44.64±2.3° | 68.64±1.5° | 63.37±4.1 | 62.35±2.6 |

*P<0.05 VS CONTROL CaCo2 AND °P<0.05 VS CONTROL CaCo2+LPS

*FIG. 1*

|  | % CD1+ / CD80+ | % CD1+ / CD86+ | % CD1+ / CD40 | % CD1+ / MHC-II |
|---|---|---|---|---|
| CONTROL MICE | 8.27±0.13 | 8.15±1.03 | 9.66±0.76 | 11.05±0.40 |
| MICE + L. paracasei CBA-L74 ALIVE | 6.99±0.51 | 7.28±1.07 | 6.04±0.84 | 14.75±0.85 |
| MICE + L. paracasei CBA-L74 INACTIVATED | 8.76±0.34 | 8.76±0.95 | 7.46±0.89 | 16.98±0.63 |

FIG. 10

|  | % CD1+ / CD80+ | % CD1+ / CD86 | % CD1+ / CD40 | % CD1+ / MHC-II |
|---|---|---|---|---|
| CONTROL MICE | 8.27±0.13 | 8.15±1.03 | 9.66±0.76 | 11.05±0.40 |
| MICE + RICE (100 mg) | 8.16±0.13 | 7.80±1.03 | 19.19±0.76 | 12.31±0.40 |
| MICE + FERMENTED RICE (100 mg) | 9.03±0.51 | 2.24±1.07 | 14.32±0.84 | 18.46±0.85 |
| MICE + RICE (500 mg) | 8.32±0.51 | 8.94±0.73 | 9.01±0.34 | 13.05±0.82 |
| MICE + FERMENTED RICE (500 mg) | 15.95±0.43 | 7.18±0.95 | 13.84±0.89 | 32.83±0.93 |

*FIG. 26*

|  | CONTROL | LPS | CpG |
|---|---|---|---|
| CONTROL MICE | 20.86±0.43 | 25.01±0.83* | 23.56±0.74* |
| MICE + RICE | 19.3±0.21 | 24.21±0.75* | 22.03±0.88* |
| MICE + FERMENTED RICE (100 mg) | 27.4±0.51 | 21.7±0.97 | 23.71±1.40 |
| MICE + FERMENTED RICE (500 mg) | 22.01±0.74 | 23.21±0.54 | 20.67±0.92 |

FIG. 27

PROBIOTIC COMPOSITIONS AND METHODS

CROSS-REFERENCE TO RELATED APPLICATIONS

This application is a divisional of U.S. application Ser. No. 16/360,154, filed Mar. 21, 2019, now U.S. Pat. No. 11,109,603, which is a continuation of U.S. application Ser. No. 15/393,904, filed Dec. 29, 2016, now U.S. Pat. No. 10,251,407, which is a divisional of U.S. application Ser. No. 14/127,573, filed Dec. 19, 2013, now U.S. Pat. No. 10,039,296, which is a national phase application of International Application No. PCT/US2012/042959, filed Jun. 18, 2012, which claims priority to U.S. Provisional Application No. 61/498,910, filed Jun. 20, 2011, which are incorporated by reference herein in their entireties.

FIELD OF THE INVENTION

The present invention relates to probiotic organisms, food products prepared with probiotic organisms and pharmaceutical compositions comprising probiotic organisms. These compositions are useful in stimulating the mucosal immune system and for treatment of disorders associated with immaturity of the mucosal immune system.

BACKGROUND OF THE INVENTION

The intestinal epithelium is constantly exposed to foreign materials that can be either harmful or beneficial to the host. As a result, the intestinal immune system must strike a delicate balance between: 1) protective immune responses that are induced by intestinal pathogens or toxins and 2) avoidance of immune responses against both food antigens and the $10^{14}$ commensal beneficial microorganisms that normally reside in the gut. Disruption of either the protective responses or the tolerance responses can result in a wide array of disorders including, for example, infections, inflammation, food allergies, food hypersensitivity, inflammatory bowel disease, Crohn's disease, celiac disease, periodontal disease, rheumatoid arthritis, atherosclerosis and colon cancer.

The immunoregulatory network comprising the intestinal immune system changes with age. The network is poorly developed in human newborns and is established gradually over the first few years of life. The immaturity of the immune system plays a role in the prevalence of infections and food-related disorders in infants and young children. Conversely, the ability of the intestinal immune system to respond to new challenges declines in the elderly.

Gastrointestinal disorders, for example, infections, inflammatory disorders and food-related disorders such as food allergies, food intolerance or food hypersensitivity have a significant impact on the health and quality of life in both children and adults. Infectious gastroenteritis is the most common pediatric gastrointestinal disorder. About 1 billion episodes occur worldwide each year, most commonly in developing countries among children under 5 years of age. Worldwide death rates for infectious gastroenteritis average from 3 to 6 million children per year. In the United States, 25 to 35 million new cases occur annually, resulting in 300 to 400 deaths. In addition, infectious gastroenteritis in the US results in an estimated 200,000 hospitalizations and 1.5 million outpatient visits at a cost in excess of 1 billion dollars. Food-related disorders such as allergies also have a substantial effect on health or both children and adults.

Symptoms of food allergies can vary depending upon the severity of the allergy and can range from a mild tingling sensation around the mouth and lips to life-threatening anaphylaxis. It is estimated that food allergies affect between 1-10% of the population in the U.S. The Center for Disease Control found that in 2007, approximately 3 million children under age 18 years (3.9%) were reported to have a food or digestive allergy in the previous 12 months. For some children, food allergies become less severe with age, for others, they remain a lifelong concern. Infants who suffer from allergy early in life may develop "allergic march." For example, many individuals who have severe allergic reactions to cow's milk in infancy at risk for the development of asthma later in childhood. There are indications that the prevalence of food allergies is increasing worldwide.

Regardless of the etiology, gastrointestinal disorders not only adversely affect a child's health, but can have a serious impact on family economics, social interactions and school and parental work attendance. There is a continuing need for therapeutic strategies that promote gastrointestinal health, particularly in individuals who are risk for or who suffer from gastrointestinal disorders.

SUMMARY OF THE INVENTION

The present invention provides compositions comprising a fermented food product, wherein the food product has been fermented by the probiotic bacterium, *Lactobacillus paracasei* CBA L74, International Depository Accession Number LMG P-24778. The food product can be a dairy product or a cereal product. Also provided are compositions comprising the probiotic bacterium, *Lactobacillus paracasei* CBA L74, International Depository Accession Number LMG P-24778 and a physiologically acceptable carrier. The physiologically acceptable carrier can be a food product or a pharmaceutical carrier. Also provided are methods of making a nutritional composition, the method comprising: providing a food product; combining the food product with an effective amount of the probiotic bacterium, *Lactobacillus paracasei* CBA L74, International Depository Accession Number LMG P-24778 and, optionally, a co-inoculum, to form a mixture; and incubating the mixture at a temperature and for a time sufficient for fermentation to occur. The nutritional composition may be dried. The nutritional composition may be combined with one or more additional food products. For any of the compositions and methods described herein, the *Lactobacillus paracasei* CBA L74 cells can be subjected to treatments that render them non-replicating. The concentration of *Lactobacillus paracasei* CBA L74 in the compositions can vary depending upon the intended use, e.g., as a nutritional composition or a pharmaceutical composition. Useful ranges include the equivalent of about $1 \times 10^2$ colony-forming units per gram ("cfu/g") to about $1 \times 10^{12}$ colony-forming units per gram ("cfu/g") dry weight.

Also provided are methods of treating a subject at risk for a developing a gastrointestinal disorder, the method comprising: identifying a subject at risk for a gastrointestinal disorder; administering an effective amount of a composition comprising a food product wherein the food product has been fermented by the probiotic bacterium, *Lactobacillus paracasei* CBA L74, International Depository Accession Number LMG P-24778. The gastrointestinal disorder can be a mucosal immune system deficit, for examine, an immature immune system, a food allergy, a disorder associated with diarrhea, a bacterial or viral infection, irritable bowel syndrome, inflammatory bowel disease, Crohn's disease, necrotizing enterocolitis or aging, particularly aging of the gastrointestinal system.

Also provided are methods of treating a subject having a gastrointestinal disorder. The methods include: identifying a subject having a gastrointestinal disorder; administering an effective amount of a composition comprising a food product wherein the food product has been fermented by the probiotic bacterium, Lactobacillus paracasei CBA L74, International Depository Accession Number LMG P-24778. In some embodiments, the methods include: identifying a subject having a gastrointestinal disorder; administering an effective amount of a pharmaceutical composition comprising the probiotic bacterium, Lactobacillus paracasei CBA L74, International Depository Accession Number LMG P-24778. The gastrointestinal disorder can be a mucosal immune system deficit, for examine, an immature immune system, a food allergy, a disorder associated with diarrhea, a bacterial or viral infection, irritable bowel syndrome, inflammatory bowel disease, Crohn's disease or necrotizing enterocolitis.

Also provided are and methods of modulating the immune system in a subject. The methods include: identifying a subject in need of immune system modulation and administering an effective amount of a composition comprising a food product wherein the food product has been fermented by the probiotic bacterium, Lactobacillus paracasei CBA L74, International Depository Accession Number LMG P-24778.

Articles of manufacture are also provided. These can include kits comprising a measured amount of a nutritional composition comprising a fermented food product, wherein the food product has been fermented by the probiotic bacterium, Lactobacillus paracasei CBA L74, International Depository Accession Number LMG P-24778 and one or more items selected from the group consisting of packaging material, a package insert comprising instructions for use, a sterile fluid, and a sterile container. In some embodiments, the kit can include a measured amount of a pharmaceutical composition comprising Lactobacillus paracasei CBA L74, International Depository Accession Number LMG P-24778 and one or more items selected from the group consisting of packaging material, a package insert comprising instructions for use, a sterile fluid, and a sterile container.

The details of one or more embodiments of the invention are set forth in the accompanying drawings and the description below. Other features, objects and advantages of the invention will be apparent from the description and drawings and from the claims.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1 is a table showing an analysis of the effect of L. paracasei CBA L74 on DC cell phenotype.

FIG. 10 is a table showing an analysis of the effect of L. paracasei CBA L74 on DC phenotype in mice supplemented with L. paracasei CBA L74.

FIG. 26 is a table showing an analysis of the effect of *L. paracasei* CBA L74 on DC phenotype in mice supplemented with rice fermented by *L. paracasei* CBA L74.

FIG. 27 is a table showing an analysis of the effect of *L. paracasei* CBA L74 on DC phenotype after exposure to LPS or CpG in mice supplemented with rice fermented by *L. paracasei* CBA L74.

DETAILED DESCRIPTION

Figure 2A:
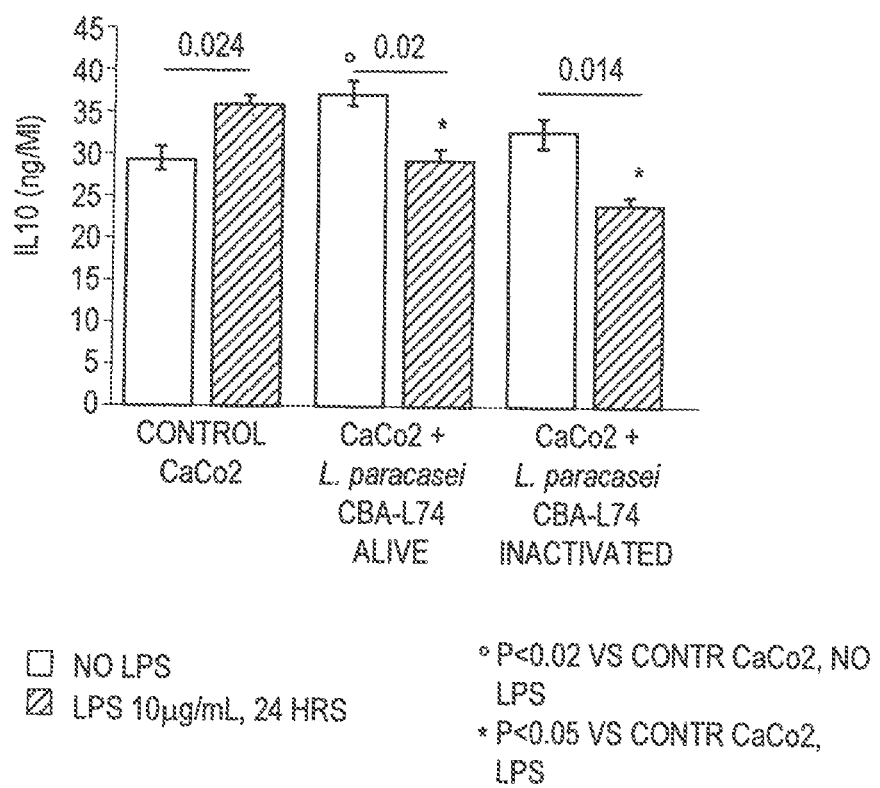
FIG. 2A is a graph depicting IL-10 production in DCs co-cultured with Caco2 exposed to L. paracasei CBA L74.

The present invention is based, in part, on the inventors' discovery that foods fermented by the probiotic organism *Lactobacillus paracasei*, strain CBA L74, can have immunomodulatory properties. This strain was isolated by the inventors and deposited under the Budapest Treaty on the International Recognition of the Deposit of Micro-organisms for the Purposes of Patent Procedure on Sep. 9, 2008 at the Belgian Coordinated Collections of Micro-organisms (BCCM) Laboratorium voor Microbiologie (LMG), Ghent, Belgium. The Accession Number given by the International Depositary Authority is LMG P-24778. For ease of reading, we will not repeat the phrase "Accession Number LMG P-24778" on every occasion. It is to be understood that where we refer to *L. paracasei*, strain CBA L74, we refer to the deposited strain having the Accession Number LMG P-24778.

The compositions of the invention include the probiotic organism, *L. paracasei* CBA L74. The World Health Organization has defined probiotics as: "Live microorganisms which when administered in adequate amounts confer a health benefit on the host." In some embodiments, the *L. paracasei* CBA L74 can be subjected to treatments that render them non-replicating, for example, exposure to heat, dessication, y-irradiation, or uv-irradiation. A non-replicating *L. paracasei* CBA L74 can be a dead cell or a living cell that has been rendered incapable of cell division. A non-replicating *L. paracasei* CBA L74 can be an intact cell or a cell that has undergone partial or complete lysis. In some embodiments, the non-replicating cells can include a mixture of intact and lysed cells.

While we believe we understand certain events that occur upon administration of compositions comprising or made by fermentation with *L. paracasei* CBA L74, the compositions of the present invention are not limited to those that work by affecting any particular cellular mechanism. Our working hypothesis is that probiotic organisms or compositions fermented with probiotic organisms may provide an increased barrier to translocation of bacteria and bacterial products across mucosa, competitively exclude potential pathogens, modify of host response to microbial products, and enhance enteral nutrition in ways that inhibits the growth of pathogens. The beneficial effects of compositions comprising non-replicating probiotic organisms may derive for example, from metabolites produced during fermentation, for example, organic acids such as lactic acid, butyric acid or acetic acid. Alternatively or in addition, microbial DNA, e.g., unmethylated CpG dinucleotides, bacterial cell wall fragments and other sub-cellular bacterial components, such as proteins, carbohydrates and lipids, may exert immuno-modulatory effects on the mucosal immune system.

The inventors have found that isolated *L. paracasei* CBA L74 modulated the levels of both pro- and anti-inflammatory markers when assayed in vitro and in vivo. Moreover, immunomodulatory effects were also observed following administration of foods that had been fermented by *L. paracasei* CBA L74. Such immunomodulatory effects were noted even when the fermented foods had been treated, e.g., by heat, to render the *L. paracasei* CBA L74 non-replicating. Accordingly, the invention features compositions and methods that can be used to stimulate the intestinal immune system. The compositions can include food products that have been fermented by *L. paracasei* CBA L74. The food products can be any of a wide range of foods that are amenable to fermentation by *L. paracasei* CBA L74. In some embodiments, the compositions can include isolated *L. paracasei* CBA L74 and a physiological carrier. The carrier may be a food product, but the invention is not so limiting and in some embodiments the carrier may be a pharmacological carrier. Also provided are methods of making and using the compositions. The methods of the invention include methods of producing compositions comprising *L. paracasei* CBA L74, methods of fermenting food products with *L. paracasei* CBA L74 and methods of administering the compositions to generate an immunomodulatory response in a subject. The compositions may be administered to a subject having an immature immune system, a subject at risk for a gastrointestinal disorder or who has a gastrointestinal disorder. The methods can be used on human subjects, for example, infants and children, or in veterinary medicine. Regardless of the subject (whether human or non-human), any of the present methods can include a step of identifying the subject. For example, the methods can include a step of determining whether the subject is in need of treatment.

Compositions

Fermented Foods

The compositions of the invention include nutritional compositions, i.e., food products fermented by the probiotic organism, *L. paracasei* CBA L74. Any food product amenable to fermentation by *L. paracasei* CBA L74 may be used. The food product can be a dairy product, for example, milk or a milk-based product. Exemplary milk sources include, without limitation, cattle, sheep, goats, yaks, water buffalo, horses, donkeys, reindeer and camels. Regardless of the source, the milk or milk products can be in any form suitable for fermentation by *L. paracasei* CBA L74. For example, the milk can be whole milk or milk that has been processed to remove some or all of the butterfat, e.g., 2% milk, 1% milk or no-fat milk. Alternatively or in addition, the milk can be previously pasteurized and or homogenized, dried and reconstituted, condensed or evaporated. Fractions of milk products including casein, whey protein or lactose may also be used. In some embodiments, the milk product can be from about 1% to about 30% reconstituted skim milk powder, for example about 2%, about 5%, about 7%, about 9%, about 10%, about 12%, about 15%, about 20%, about 25%, about 30% reconstituted skim milk powder. Prior to fermentation the milk product can be combined with one or more of the following: a) a carbohydrate (e.g., a disaccharide such as dextrose or a starch; b) a lipid; c) a vitamin and d) a mineral. For example, skim milk powder may be combined with dextrose to about 2%, e.g., about 0.25%, about 0.50%, about 0.75%, about 1.0%, about 1.5% or about 2.0%.

The food product can be a cereal product, for example, rice, wheat, oats, barley, corn, rye, sorghum, millet, or triticale. The cereal product can be a whole grain or be milled into a flour. The food product can be a single kind of cereal or a mixture of two or more kinds of cereals, e.g., oat flour plus malted barley flour. The cereal products can be of a grade and type suitable for human consumption or can be products suitable for consumption by domestic animals. Generally, the cereal product is hydrated prior to fermentation. The concentration of cereal can vary, but useful ranges include from about 5% to about 50% weight/volume, for example, about 8% weight/volume, about 10% weight/volume, about 12% weight/volume, about 15% weight/volume, about 18% weight/volume, about 20% weight/volume, about 22% weight/volume, about 25% weight/volume, about 30% weight/volume, about 35% weight/volume, about 40% weight/volume, about 45% weight/volume or about 50% weight/volume. Exemplary concentrations include 15% weight/volume of rice or a mixture of 18.5% weight/volume oat flour plus 5% weight/volume of malted barley flour. The pH of the hydrated cereals may be adjusted using any acid suitable for consumption. The acid can be, for example, an organic acid. Useful organic acids include acetic acid, citric acid, lactic acid, adipic acid, malic acid and tartaric acid. Any combination of two or more acids can be used. In some embodiments, the pH may be adjusted to about 4.0 using citric acid.

The food product can also be a vegetable or a fruit product, for example, a juice, a puree, a concentrate, a paste, a sauce, a pickle or a ketchup. Exemplary vegetables and fruits include, without limitation, squashes, e.g., zucchini, yellow squash, winter squash, pumpkin; potatoes, asparagus, broccoli, Brussels sprouts, beans, e.g., green beans, wax beans, lima beans, fava beans, soy beans, cabbage, carrots, cauliflower, cucumbers, kohlrabi, leeks, scallions, onions, sugar peas, English peas, peppers, turnips, rutabagas, tomatoes, apples, pears, peaches, plums, strawberries, raspberries, blackberries, blueberries, lingonberries, boysenberries, gooseberries, grapes, currants, oranges, lemons, grapefruit, bananas, mangos, kiwi fruit, and carambola.

The food product can also be a "milk" made from grains (barley, oat or spelt "milk") tree nuts (almond, cashew, coconut, hazelnut or walnut "milk"), legumes (soy, peanut, pea or lupin "milk") or seeds (*quinoa*, sesame seed or sunflower seed "milk").

Also contemplated are food products comprising animal proteins, for example, meat, for example, sausages, dried meats, fish and dried fish products.

Regardless of the type of food product that is used, the product is combined with *L. paracasei* CBA L74 and incubated at a temperature and for a time sufficient for fermentation to occur. Any standard fermentation method known in the art may be used. Specific fermentation conditions will vary according to many factors including, for example, the type of food product, the concentration of the food product, the instrumentation that is used, the sample volume, the initial concentration of the *L. paracasei* CBA L74 inoculum, the presence, if any, of a co-inoculum, the organoleptic properties of the fermented food, and the intended use of the fermented food.

Both the instrumentation and the substrate (i.e., the food product to be fermented) are sterilized prior to inoculation with *L. paracasei* CBA L74 in order to decrease the level of, or eliminate, viable bacteria and/or fungi and/or infectious viruses. The instrumentation can be sterilized using standard methods or according to the manufacturer's instructions. Choice of a particular method for sterilization of the substrate will depend, in part, on the stability of the substrate to the sterilization method. For example, the substrate can be sterilized by steam and pressure, e.g. by autoclaving, repeated cycles of heating and cooling (e.g., tyndalization) exposure to high pressures (e.g., pascalization), ultrafiltration, or radiation (e.g., exposure to gamma-, x-, e-beam, and/or ultra-violet (wavelength of 10 nm to 320 nm, e.g., 50 nm to 320 nm, 100 nm to 320 nm, 150 nm to 320 nm, 180 nm to 320 nm, or 200 nm to 300 nm). Aliquots of the substrate can be removed following treatment and plated on suitable media to confirm the absence of bacterial and/or fungal contaminants. If the substrate has been sterilized by exposure to high temperatures, it should be cooled to at least 37° C. prior to inoculation with *L. paracasei* CBA L74.

The substrate can be inoculated with *L. paracasei* CBA L74 according to standard methods, for example, from fresh liquid culture or a freeze-dried culture that has been resuspended in aqueous medium for a short time prior to inoculation. In general, *L. paracasei* CBA L74 are added at concentrations of about $0.5 \times 10^6$ to about $1 \times 10^6$ cfu/ml of substrate, e.g., about $1 \times 10^6$ cfu/ml, about $2 \times 10^6$ cfu/ml, about $5 \times 10^6$ cfu/ml, $7 \times 10^6$ cfu/ml $8 \times 10^6$ cfu/ml. The culture should be agitated sufficiently to produce a relatively uniform distribution of bacteria and substrate, but not excessively since *L. paracasei* CBA L74 is an anaerobic bacterium. For example, a five liter culture may be agitated at about 150 rpm. Fermentation temperature is generally at 37° C. Various parameters, for example, the pH, the partial pressure of $O_2$, stirrer speed, temperature, gas mixing, foam level and substrate concentration can be monitored during fermentation and adjusted accordingly. Growth of the *L. paracasei* CBA L74 can be monitored using standard microbiological methods. Fermentation is carried out until the concentration of *L. paracasei* CBA L74 is about between about $10^8$/ml and about $10^9$/ml. Depending upon the substrate and other conditions, this concentration may be reached in about 10 to about 30 hours after inoculation, e.g., about 12 hours, about 15 hours, about 18 hours, about 24 hours, about 30 hours.

Samples of the substrate can be assayed before, during and after fermentation for quality assurance using standard microbiological methods. Exemplary methods include, but are not limited to, growth on Rogosa agar for *L. paracasei* CBA L74, growth on plate count agar (PCA) for total aerobes, growth on McConkay agar for coliforms, growth on reinforced clostridial agar (RCM) for Clostridia. In addition to colony counts, colony morphologies can be observed and compared to reference samples.

In some embodiments, a co-inoculum can be added along with the *L. paracasei* CBA L74 in order to help initiate fermentation. Useful co-inocula for fermentation of milk products include, for example, without limitation, *Streptococcus thermophilus, Lactobacillus paracasei, Lactobacillus salivarious, Lactobacillus rhamnosus, Lactobacillus casei, Lactobacillus lactis, Lactobacillus delbrueckii*, subsp. *Bulgaricus, Lactobacillus acidophilus, Lactobacillus brevis*, or *Leuconostoc mesenteroides*. In general, the concentration of the co-inoculum will be lower than that of *L. paracasei* CBA L74, for example, about $1 \times 10^4$/ml$\times 10^5$/ml. The final concentration of *S. thermophilus* can range from about $0.5 \times 10^8$/ml to about $2.5 \times 10^8$/ml.

Food Products

Once suitable concentrations of *L. paracasei* CBA L74 have been reached, the fermented food can be further processed for use. In some embodiments, the pH of the fermented food can be adjusted, for example from about 3.0 to nearer to neutrality, e.g., 6.5, with the addition of NaOH or KOH. In some embodiments the fermented food can be dried. The fermented food product can be dried by any method known in the art that will result in the retention of immunomodulatory properties of the fermented food. Exemplary drying methods include spray drying, freeze-drying e.g., lyophilization, or drum-drying. The final water content of the fermented food product may vary but can be between about 1% and about 10% or more. In some embodiments, the drying process can render the *L. paracasei* CBA L74 non-replicating.

The dried fermented foods can be hydrated before use. Depending on the amount of liquid used in the hydration, the fermented food products may contain the equivalent of about $10^2$ and $10^{12}$ cfu/ml of *L. paracasei* CBA L74. The dried *L. paracasei* CBA L74 do not form colonies, so it is understood that this amount is calculated based on the number of live bacteria that were present in the fermented foods prior to the drying step. In some embodiments, the fermented food products may include the equivalent of about $10^7$ to about $10^{12}$ cfu/g, e.g., about $5 \times 10^7$ cfu/g, about $1 \times 10^8$ cfu/g, about $5 \times 10^8$ cfu/g, about $1 \times 10^9$ cfu/g, about $5 \times 10^9$ cfu/g, about $1 \times 10^{10}$ cfu/g, about $5 \times 10^{10}$ cfu/g, about $1 \times 10^{11}$ cfu/g, about $5 \times 10^{11}$ cfu/g of dry weight.

Two or more fermented food products prepared by the methods of the invention may be combined prior to administration. For example, fermented milk products may be combined with fermented cereal products. Alternatively, the fermented food product can be combined with other food products, for example, non-fermented food products or food products fermented using other bacterial strains. Any combination can be used provided that the immunomodulatory properties of the fermented food are retained. Exemplary food products include, without limitation, dairy products, e.g., milk, yoghurt, curd, cheese and cheese-based products, fermented milks, milk-based fermented products, milk-based powders, infant formulae, milk-based strained infant foods, ice cream, gelato, puddings, soups, sauces, purees, or dressings, nutritional formulas for the elderly; cereal products e.g., pablum, cereal-based strained infant foods, oatmeal, farina, semolina, polenta, pasta, biscuits, crackers, energy bars; vegetable products, e.g., purees, vegetable-based strained infant foods, pickled vegetables including cucumbers, cabbage, carrots, beans, peppers, or relishes; fruit products, e.g., fruit-based strained infant foods, tomato products, purees, sauces, pastes, ketchups, fruit purees; or a protein-based products, e.g., legumes, sausages, lunch meats, hot dogs, or pureed meats. In some embodiments the fermented food may be combined with pet foods or animal feeds.

In some embodiments, the compositions can include *L. paracasei* CBA L74 fermentates, from which all or substantially all, of the *L. paracasei* CBA L74 cells have been removed. Methods for separating cells from growth media are well known in the art and can rely upon physical methods, for example, centrifugation to produce a cell pellet and a culture supernatant, filtration, ultrafiltration, tangential flow-filtration, normal flow filtration or reverse osmosis. Alternatively or in addition, the separation method can be ligand-based and include, for example, an antibody that specifically binds to *L. paracasei* CBA L74. The antibody can be coupled to a solid support such as a magnetic bead.

Isolated *L. paracasei* CBA L74

In some embodiments, the compositions of the invention include *L. paracasei* CBA L74 that are partially or substantially isolated from the media in which they were grown. The *L. paracasei* CBA L74 can be live or non-replicating, e.g., inactivated, for example, by heat-treatment. The cells can be lyophilized or freeze-dried under conditions that preserve cell viability. Methods of lyophilization are well known in the art.

Physiological Carriers

In some embodiments, the compositions of the invention may include isolated *L. paracasei* CBA L74 in combination with a physiologically acceptable carrier. The *L. paracasei* CBA L74 can be live or non-replicating, e.g., inactivated, for example, by heat-treatment. The dosage may vary, but can range from the equivalent of about $10^2$ to about $10^{12}$ cfu/g, e.g., $1 \times 10^2$ cfu/g, $5 \times 10^2$ cfu/g, $1 \times 10^3$ cfu/g, $5 \times 10^3$ cfu/g, $1 \times 10^4$ cfu/g, $5 \times 10^4$ cfu/g, $1 \times 10^5$ cfu/g, $5 \times 10^5$ cfu/g, $1 \times 10^6$ cfu/g, $5 \times 10^6$ cfu/g, $1 \times 10_7$ cfu/g, $5 \times 10_7$ cfu/g, $1 \times 10^8$ cfu/g, $5 \times 10^8$ cfu/g, $1 \times 10^9$ cfu/g, $5 \times 10^9$ cfu/g, $1 \times 10^{10}$ cfu/g, $5 \times 10^{10}$ cfu/g, $1 \times 10^{10}$ cfu/g, $5 \times 10^{11}$ cfu/g, $1 \times 10^{12}$ cfu/g of dry weight.

The physiologically acceptable carrier can be a food or food product. Isolated *L. paracasei* CBA L74 can be added to a food or food product prior to packaging or processing. Alternatively or in addition, isolated *L. paracasei* CBA L74 can be added to a food or food product prior to consumption. For example, isolated *L. paracasei* CBA L74 can be combined with any of the foods or food products described above. The food product can be a fermented food product or an unfermented food product. For example, isolated *L. paracasei* CBA L74 can be added to an unfermented dairy or cereal product. In some embodiments, the *L. paracasei* CBA L74 can be added to a food or food product to include the equivalent of about $10^7$ to about $10^{12}$ cfu/g, e.g., about $5 \times 10^7$ cfu/g, about $1 \times 10^8$ cfu/g, about $5 \times 10^8$ cfu/g, about $1 \times 10^9$ cfu/g, about $5 \times 10^9$ cfu/g, about $1 \times 10^{10}$ cfu/g, about $5 \times 10^{10}$ cfu/g, about $1 \times 10^{11}$ cfu/g, about $5 \times 10^{11}$ cfu/g of dry weight.

Pharmaceutical Carriers

The compositions also include a pharmaceutically acceptable carrier. We use the terms "pharmaceutically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

This invention also includes pharmaceutical compositions which contain, as the active ingredient, the *L. paracasei* CBA L74 described herein, in combination with one or more pharmaceutically acceptable carriers. In some embodiments, the *L. paracasei* CBA L74 can be sterilized using conventional sterilization techniques before or after it is combined with the pharmaceutically acceptable carrier. In making the compositions of the invention, the *L. paracasei* CBA L74 is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. As is known in the art, the type of diluent can vary depending upon the intended route of administration. The resulting compositions can include additional agents, such as preservatives. The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formulary). Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

Pharmaceutically acceptable compositions for use in the present methods, including those in which *L. paracasei* CBA L74 is entrapped in a colloid for oral delivery, can be prepared according to standard techniques. The *L. paracasei* CBA L74 can be dried and compacted by grinding or pulverizing and inserted into a capsule for oral administration. In some embodiments, the *L. paracasei* CBA L74 can be combined one or more excipients, for example, a disintegrant, a filler, a glidant, or a preservative. Suitable capsules include both hard shell capsules or soft-shelled capsules. Any lipid based or polymer-based colloid may be used to form the capusule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment. In some embodiments, the capsule does not include gelatin. In other embodiments, the capsule does not include plant polysaccharides or their derivatives.

Regardless of their original source or the manner in which they are obtained, the *L. paracasei* CBA L74 of the invention can be formulated in accordance with their use. These compositions can be prepared in a manner well known in the pharmaceutical art, and can be administered by a variety of routes, depending upon whether local or systemic treatment is desired and upon the area to be treated. Administration may be oral or topical (including ophthalmic and to mucous membranes including intranasal, vaginal and rectal delivery). In some embodiments, administration can be pulmonary (e.g., by inhalation or insufflation of powders or aerosols, including by nebulizer; intratracheal, intranasal, epidermal and transdermal) or ocular. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

The compositions can be formulated in a unit dosage form, each dosage containing, for example, from about 0.005 mg to about 2000 mg of *L. paracasei* CBA L74 per daily dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the *L. paracasei* CBA L74 of the present invention.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The proportion or concentration of the compositions of the invention in a pharmaceutical composition can vary depending upon a number of factors including dosage, chemical characteristics (e.g., hydrophobicity), and the route of administration. For example, the *L. paracasei* CBA L74 of the invention can be provided in a capsule containing from about 0.005 mg gram to about 1000 mg for oral administration. Alternatively or in addition, the dosage can be expressed as cfu/g of dry weight. The dosage may vary, but can range from the equivalent of about $10^2$ to about $10^{12}$ cfu/g, e.g., $1\times10^2$ cfu/g, $5\times10^2$ cfu/g, $1\times10^3$ cfu/g, $5\times10^3$ cfu/g, $1\times10^4$ cfu/g, $5\times10^4$ cfu/g, $1\times10^5$ cfu/g, $5\times10^5$ cfu/g, $1\times10^6$ cfu/g, $5\times10^6$ cfu/g, $1\times10^7$ cfu/g, $5\times10^7$ cfu/g, $1\times10^8$ cfu/g, $5\times10^8$ cfu/g, $1\times10^9$ cfu/g, $5\times10^9$ cfu/g, $1\times10^{10}$ cfu/g, $5\times10^{10}$ cfu/g, $1\times10^{11}$ cfu/g, $5\times10^{11}$ cfu/g, $1\times10^{12}$ cfu/g of dry weight.

Methods of Use

The compositions disclosed herein are generally and variously useful for stimulation of an immunomodulatory response in the mucosal immune system. Subjects for whom such stimulation is beneficial include those have a mucosal immune system deficit, for example, those having an immature immune system, such as infants or small children, those having a depressed immune system, such as the elderly, patients taking immunosuppressive drugs, radiation or chemotherapy, those having a hyperactivated immune system due to allergies or autoimmune disorders and those suffering from gastrointestinal disorders. Gastrointestinal disorders can include infections due to viruses, e.g., rotaviruses; pathogenic bacteria, e.g., *Salmonella, Yersinia, Shigella, Listeria, Clostridium, E. coli, E. sakazaki, H. pylori*; or pathogenic protozoa, e.g., *Entamoeba histolytica, Cryptosporidium* spp, *Campylobacter* spp. Gastrointestinal disorders can also include, for example, food allergies, food hypersensitivity, irritable bowel syndrome, inflammatory bowel disease, pouchitis, Crohn's disease, ulcerative colitis, celiac disease, necrotizing enterocolitis, and aging, particularly aging of the gastrointestinal system, A subject is effectively treated whenever a clinically beneficial result ensues. This may mean, for example, a complete resolution of the symptoms associated with a mucosal immune system deficit, a decrease in the severity of the symptoms associated with a mucosal immune system deficit, or a slowing of the progression of symptoms associated with a mucosal immune system deficit. These methods can further include the steps of a) identifying a subject (e.g., a patient and, more specifically, a human patient) who has a mucosal immune system deficit; and b) providing to the subject a composition comprising *L. paracasei* CBA L74 described herein, such as any fermented food product or composition comprising *L. paracasei* CBA L74 in a physiologically acceptable carrier. An amount of such a composition provided to the subject that results in a complete resolution of the symptoms associated with a mucosal immune system deficit, a decrease in the severity of the symptoms associated with a mucosal immune system deficit, or a slowing of the progression of symptoms associated with a mucosal immune system deficit is considered a therapeutically effective amount. The present methods may also include a monitoring step to help optimize dosing and scheduling as well as predict outcome.

The methods disclosed herein can be applied to a wide range of species, e.g., humans, non-human primates (e.g., monkeys), horses, pigs, cows or other livestock, dogs, cats or other mammals kept as pets, rats, mice, or other laboratory animals. The compositions described herein are useful in therapeutic compositions and regimens or for the manufacture of a medicament for use in treatment of conditions as described herein (e.g., a mucosal immune system deficit due to immaturity, aging, infection, food allergies, an inflammatory or autoimmune disorder.)

The nutritional compositions described herein can be administered orally as part of the ordinary daily diet of a subject. The food compositions may be administered as nutritional support to both children and adults. When formulated as pharmaceuticals, the compositions can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

Regardless of whether the compositions are formulated as food products or as pharmaceuticals, the dosage required will depend on the route of administration, the nature of the formulation, the nature of the subject's condition, e.g., immaturity of the immune system or a gastrointestinal disorder, the subject's size, weight, surface area, age, and sex, other drugs being administered, and the judgment of the attending clinicians. Suitable dosages are in the range of 0.01-1.000 mg/kg. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems. For example, in vitro analysis of cytokine production by peripheral blood mononuclear cells (PBMCs) can be a useful for assaying pro- and anti-inflammatory responses, e.g., secretion of IL-1$\beta$, IL-12, IL-4, TNF-$\alpha$, or IL-10 respectively. Compositions can also be analyzed for effects in animal models, for example, IgA production, cytokine production by explants of Peyer's patches, and dendritic cell and T-cell responses.

Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a composition can be administered once a week (for, for example, 4 weeks to many months or years); once a month (for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly. When the compositions are formulated as food product, for example, the compositions can be administered daily at every meal.

Any method known to those in the art can be used to determine if a particular response is induced. Clinical methods that can assess the degree of a particular disease state can be used to determine if a response is induced. For example, a subject can be monitored for symptomatic relief, e.g., relief from colic, diarrhea, constipation, nausea, vomiting, abdominal pain, cramping, heartburn, abdominal distention, flatulence, or incontinence. Alternatively or in addition, serum markers, imaging techniques, e.g., ultrasound, x-rays, and endoscopic methods can be used.

The compositions may also be administered in conjunction with other therapeutic modalities. Other therapeutic modalities will vary according to the particular disorder, but can include, for example, anti-diarrhea medications, anti-emetics, anti-cholinergic agents, anti-inflammatory agents, antibiotics anti-histamines and other dietary treatments, for example, hypoallergenic infant formulas. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

Articles of Manufacture

The compositions described herein can also be assembled in kits, together with instructions for use. Accordingly, packaged products (e.g., containers containing one or more of the *L. paracasei* CBA L74 compositions described herein and packaged for storage, shipment, or sale at concentrated or ready-to-use concentrations) and kits, including at least one compound of the invention and instructions for use, are also within the scope of the invention. In any of the packaged products or kits, the *L. paracasei* CBA L74 compositions can include *L. paracasei* CBA L74 that have been rendered non-replicating. For example, the kits can include measured amounts of a nutritional composition including one or more food products fermented with *L. paracasei* CBA L74. The instructions for use can be conveyed by any suitable media. For example, they can be printed on a paper insert in one or more languages or supplied audibly or visually (e.g., on a compact disc). The packaging materials can include packaging materials, for example, vials, packets, containers. In some embodiments, the kits can include measured amounts of a composition comprising *L. paracasei* CBA L74 in a physiologically acceptable carrier along with packaging materials and instructions for use in any of the formats described above. In some embodiments, the kits can include containers containing one or more *L. paracasei* CBA L74 compositions, e.g., *L. paracasei* CBA L74 and a pharmaceutical carrier, and one or more of a suitable stabilizer, carrier molecule, flavoring, and/or the like, as appropriate for the intended use. A product can include a container (e.g., a vial, jar, bottle, bag, or the like) containing one or more *L. paracasei* CBA L74 compositions. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The components of the kit may be suitable for immediate use. The compounds can be ready for administration (e.g., present in dose-appropriate units), and may include a pharmaceutically acceptable adjuvant, carrier or other diluent and/or an additional therapeutic agent. The invention encompasses kits, however, that include concentrated formulations and/or materials that may require dilution prior to use. Alternatively, the compounds can be provided in a concentrated form with a diluent and instructions for dilution. The components of the kit may be suitable for immediate use. The invention encompasses kits, however, that include concentrated formulations and/or materials that may require dilution prior to use.

EXAMPLES

Example 1: Isolation and Characterization of *L. paracasei* CBA L74

We analyzed different strains of Lactobacilli for their ability to ferment aqueous suspensions containing different concentrations of rice flour or wheat flour. *L. paracasei* CBA L74 was selected for further analysis based on the low pH values and high CFU counts. This strain was deposited under the Budapest Treaty on the International Recognition of the Deposit of Micro-organisms for the Purposes of Patent Procedure on Sep. 9, 2008 at the Belgian Coordinated Collections of Microorganisms (BCCM) Laboratorium voor Microbiologie (LMG), Ghent, Belgium. The Accession Number given by the International Depositary Authority is LMG P-24778.

Example 2: Preparation of *L. paracasei* CBA L74 Fermented Milk

Conditions:
Substrate: 9% reconstituted skim milk powder, dextrose added at 0.25%
Substrate heat treatment: UHT—135° C. for 3 s or equivalent $F_0$
Co-Inoculum: $5\times10^6$ for *Lactobacillus paracasei* CBA-L74
  $5\times10^4$ for *Streptococcus thermophilus* (as starter of the fermentation)
Fermentation Temperature: 37° C.
Fermentation time: 15 h hours pH during fermentation: no adjustment
At the end of the fermentation pH adjustment to 6.5 with NaOH solution
Spray drying with inlet temperature 190° C. and outlet temperature 90° C.
Analysis: Cells count on the fermentate to determine *Streptococcus* thermophiles and *Lactobacillus paracasei* CBA-L74

Plating: Lactobacilli selective agar (LBS) was used for detection of *Lactobacillus paracasei* CBA-L74. L-M17 agar was used for *Streptococcus thermophilus* counts. Both were incubated at 37° C. anaerobically. Plate count agar (PCA) was used for detection of contaminants and incubated at 30° C. aerobically.

Fermentation: *L. paracasei* CBA L74 and *S. thermophilus* 1773 co-inoculum were added as fresh cultures. Fermentation was carried out for 15 hours, to a concentration of $10^8$ cfu/ml of *L. paracasei* CBA-L74. The initial pH was 6.6. At the end of the fermentation the pH was 5.1. The pH was adjusted to 6.5 by adding 2.5N NaOH. The initial concentration of *L. paracasei* CB-74 was $5\times10^6$ CFU/ml; the final concentration was more than $10^8$ CFU/ml. The initial concentration of *Streptococcus thermophilus* was $5\times10^4$ CFU/ml; the final concentration was $1\times10^8$ CFU/ml. The initial total bacterial count on PCA was 0 in the milk prior to inoculation and at T0 and too few colonies to count (TFTC) after the 15 hour fermentation period. was $5\times10^4$ CFU/ml; the final concentration was $1\times10^8$ CFU/ml.

Drying: The fermentate was dried at an inlet temperature of 190° C. and an outlet temperature of 90° C. The moisture content of the powder after spray drying was 4.87%.

Example 3: Preparation of *L. paracasei* CBA L74 Fermented Oat and Barley Flour

We prepared a one liter solution of 18.5% (w/vol) oat flour+5% (w/w) malted barley flour, using 185 g oat flour and 9.25 g malted barley flour. The mixture of flour and water was adjusted to pH 4.00 with 0.5 M citric acid. The fermenter was sterilized by autoclaving. Then the mixture of flour+water+citric acid was added to the fermenter.

The mixture was heat-treated at 80° C. for 30 minutes then cooled down to 37° C. Three different sets of fermentations conditions were tested. All fermentations were terminated after 16 hours, a time that coincided with the end of log phase growth.

TRIAL #1: *L. paracasei* CBA L74 was added to the heat-treated cereal solution to a final concentration of $2.3\times10^6$ CFU/ml and incubated with agitation at 37° C. After 16 hours count plate in MRS was $7.6\times10^8$ UFC/ml (lactic acid bacteria); contaminants measured in PCA, MC and SB were below 1000 UFC/ml. The final pH was 3.8. After 20 hours count plate in MRS was $1.2\times10^8$ UFC/ml (lactic acid bacteria); contaminants were absent. After 24 hours count plate in MRS was $5\times10^8$ UFC/ml (lactic acid bacteria); contaminants were absent. Because log phase stop after 16 hours, it was preferable to stop fermentations at 16 hours.

TRIAL #2 (pH stabilized) This fermentation was carried out by keeping the pH at 4 using 2N NaOH *L. paracasei* CBA L74 was added to the heat-treated cereal solution to a final concentration of $2.1\times10^6$ CFU/ml and incubated with agitation at 37° C. After 16 hours count plate in MRS was $7.5\times10^8$ UFC/ml (lactic acid bacteria); contaminants measured in PCA, MC and SB were below 1000 UFC/ml.

TRIAL #3 (pH stabilized) This fermentation was carried out by keeping the pH at 4 using 2N NaOH *L. paracasei* CBA L74 was added to the heat-treated cereal solution to a final concentration of $5.1\times10^6$ CFU/ml and incubated with agitation at 37° C. After 16 hours count plate in MRS was $2.1\times10^9$ UFC/ml (lactic acid bacteria); contaminants measured in PCA, MC and SB were below 1000 UFC/ml.

Example 4: Preparation of *L. paracasei* CBA L74 Fermented Rice and Wheat Flour

We prepared a one liter solution of 15% weight/volume of rice by combining 150 g of rice and 900 ml of water. The mixture was prepared at room temperature and mixed by shaking for several minutes at 1000-1300 rpm. The rice mixture was treated by tyndalization by heating of the mixture inside the instrument at 70° C., starvation at 70° C. per 20-30 minutes, cooling at 30-37° C., starvation at 30-37° C. per 20-30 minutes, heating at 70° C., starvation at 70° C. per 20-30 minutes, cooling at the fermentation temperature (37° C.) while shaking at 150-600 rpm.

*L. paracasei* CBA L74 was added from a freeze-dried sample to a final concentration of $1\times10^6$ CFU/ml. The freeze-dried sample was resuspended in water and incubated briefly at 37° C. to activate the bacteria. After the inoculation, the mixture was homogenized by shaking briefly at 300-600 rpm; during fermentation the solution was shaken at 150 rpm. Fermentation was carried out at 37° C. for 24 hours at a p02 of <15%. Aliquots were collected at the time of inoculation (T0), at 16 hours (T16), 18 hours (T18), 21 hours (T21) and at 24 hours (T24). After fermentation, the cereal was heated to 50° C. with continuous mixing. The heated cereal was then spray dried at T $air_{in}$ 80° C., T $air_{out}$ 210° C. The final moisture content was 6%.

Samples were analyzed on Rogosa agar(+vancomycin 12 microgr./ml) (48 h at 37° C.), for quantification of the *L. paracasei* CBA L74), on PCA for total aerobes (24 h at 37° C.), on McConkay agar for coliforms and RCM agar for clostridia.

The results of this fermentation were as follows: inoculum (*L. paracasei* CBA L74): $1\times10_6(+/-\frac{1}{2}$ log) CFU/ml (on the instrument) *L. paracasei* CBA L74 concentration after 24 hours of fermentation: $1\times10^8(+/-\frac{1}{2}$ log) CFU/ml
Contaminants on PCA before inoculum: $<10^4$ CFU/ml
Contaminants on McConkay before inoculum: $<10^4$ CFU/ml
Contaminants on RCM before inoculum: <10 CFU/ml
Contaminants on PCA after inoculum: $<10^4$ CFU/ml
Contaminants on PCA after 24 hours of fermentation: $<10^4$ CFU/ml
  pH before the addition of inoculum: 6 (+/−0.20)
  pH at 16-18 hours: 3.70 (+/−0.20)
  pH at 24 hours: 3.60 (+/−0.20).

Example 5: Effects of *L. paracasei* CBA L74 on Dendritic Cells in a Caco2 Cell Coculture System We analyzed the effect of live and non-replicating *L. paracasei* CBA L74 in a co-culture of intestinal epithelial cells (Caco2 cells) and human dendritic cells (DCs). Caco2 cells were seeded on a transwell membrane and after about 3 weeks, when the trans-epithelial resistance was adequate, were supplemented with *L. paracasei* CBA L74 for 96 hours. Human DCs were differentiated from peripheral blood monocytes and seeded in the basal compartment of the co-culture chamber. The trans-epithelial resistance remained constant during the experiment.

To characterize DCs phenotype, we monitored DC cell surface expression of co-stimulatory molecules (CD80 and CD86), MHC-II and adhesion molecules (CD40) by cytofluorimetric analysis. To determine the cytokine profile produced by DCs cocultured with intestinal epithelial cells exposed to *L. paracasei* CBA L74, we collected the culture medium and quantified IL-10 and IL-12p70 by ELISA. To verify the ability of Caco2 cells exposed to *L. paracasei* CBA L74 to condition DCs to promote the proliferation of T cells we performed FACS analysis and mixed lymphocyte cultures.

As shown in the Table in FIG. 1 incubation of Caco2 cells for 24 hrs with *L. paracasei* CBA L74 alive or inactivated (thermal inactivation) modified the phenotype of co-cultured dendritic cells. Furthermore the presence of *L. paracasei* CBA L74 modulated LPS-mediated changes in DC phenotype.

Figure 2B:
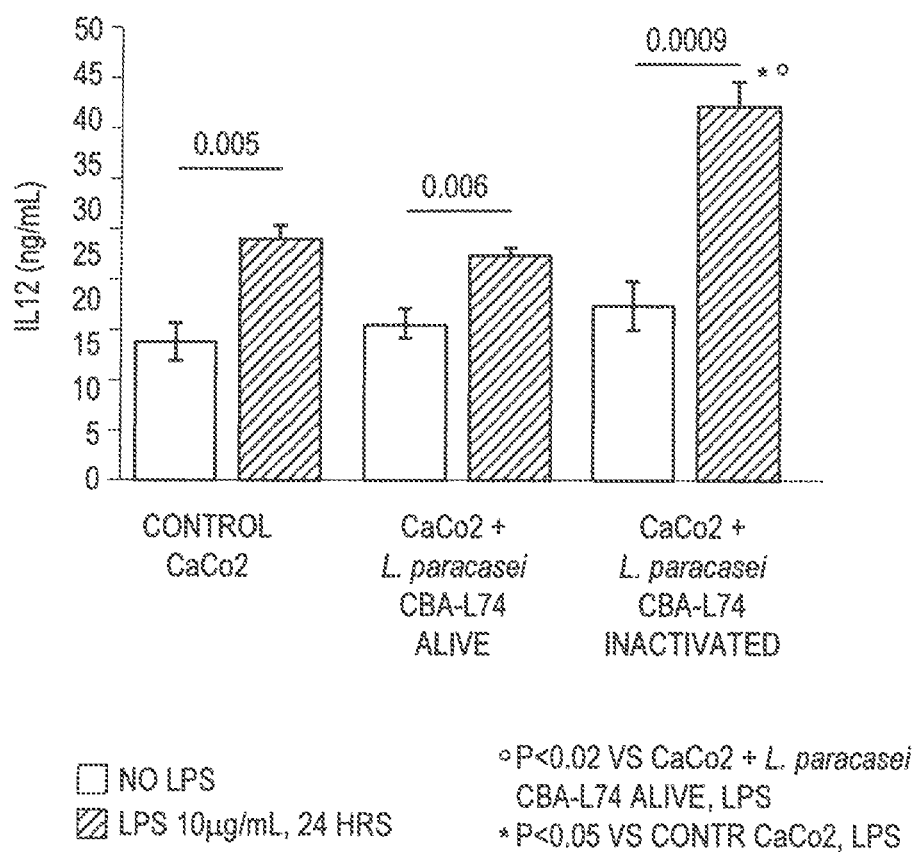
FIG. 2B is a graph depicting IL-12 production in DCs co-cultured with Caco2 exposed to L. paracasei CBA L74.

We then quantified the cytokines released from DC cocultured with Caco2 cells conditioned with *L. paracasei* (alive or inactivated). As shown in FIG. 2A, DCs co-cultured with Caco2 exposed to *L. paracasei* CBA L74 alive or inactivated showed statistically significant increase in IL-10 production. We did not observe a significant increase in IL-12 production in the absence of LPS (FIG. 2B). However, the DCs retained the ability to respond to LPS challenge by enhanced IL-12 production, suggesting that exposure to *L. paracasei* CBA L74 did not affect the overall ability of DCs to respond to pathogens.

Figure 3:
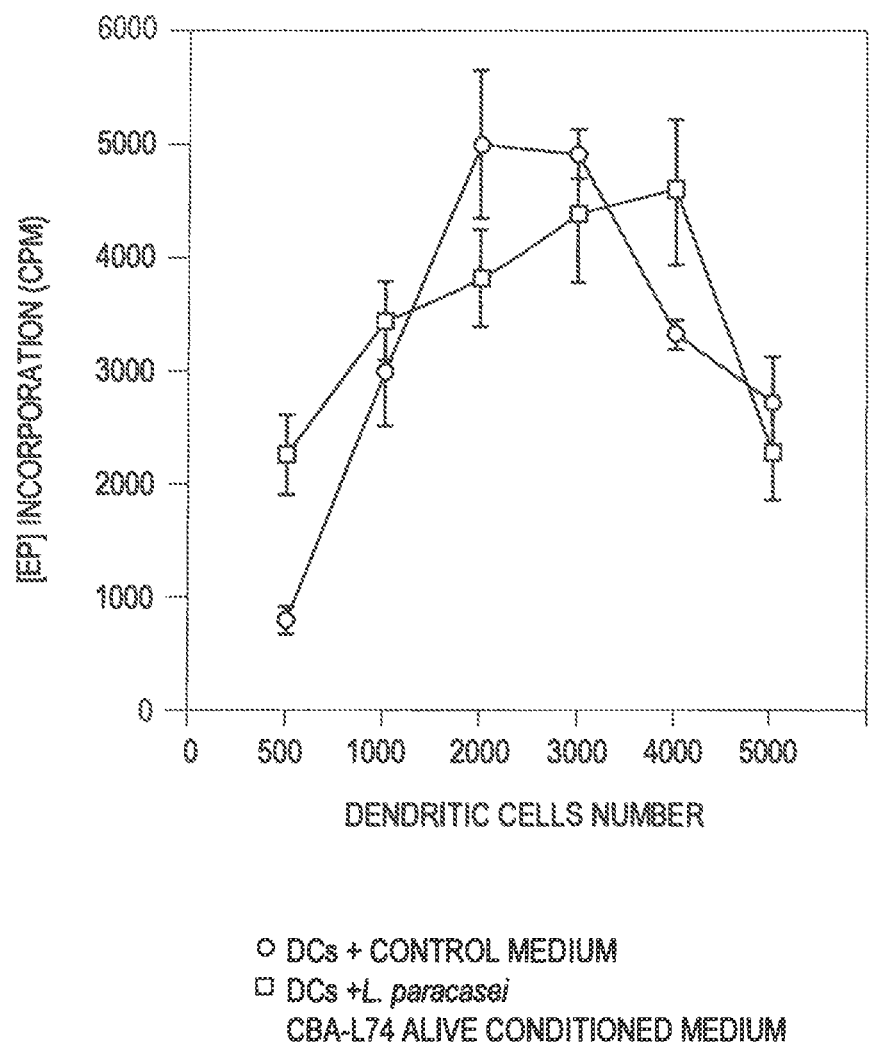
FIG. 3 is a graph depicting proliferation of T cells exposed to DCs cocultured with CaCo2 cells.

We then conducted a functional assay to verify the ability of DC exposed to CaCo2 cells cultured in presence of medium or medium supplemented with *L. paracasei* to modulate the ability of T cells to proliferate following a mixed lymphocyte reaction. As shown in FIG. 3, we did not observe significant differences in the ability of DC co-cultured with CaCo2 cells to modify T-cells proliferation.

Taken together, the in vitro data indicate that *L. paracasei* CBA L74, alive or heat inactivated, can influence the environment generated by intestinal epithelial cells that in turn modulates the activity of other immune cells such as DC. The overall picture indicates that DCs exposed to Caco2-conditioned medium reduces the expression of activation markers, produce anti-inflammatory cytokines as IL-10 while retaining the ability to respond to LPS by enhancing IL-12 production.

Example 6: Effects of *L. paracasei* CBA L74 on Morphology, Cytokine Expression and Innate Immunity in Whole Intestinal Mucosa We examined the in vivo effects by administering *L. paracasei* CBA L74 (live and heat-inactivated) as a dietary supplement in mice. After two weeks of supplementation, the animals were sacrificed and the whole intestinal mucosa was analyzed.

Mucosal morphology: We performed a haematoxylin and eosin staining of paraffin embedded ileal sections. None of the supplements had significant effects on intestinal architecture or caused an infiltrate of inflammatory cells.

Figure 4:
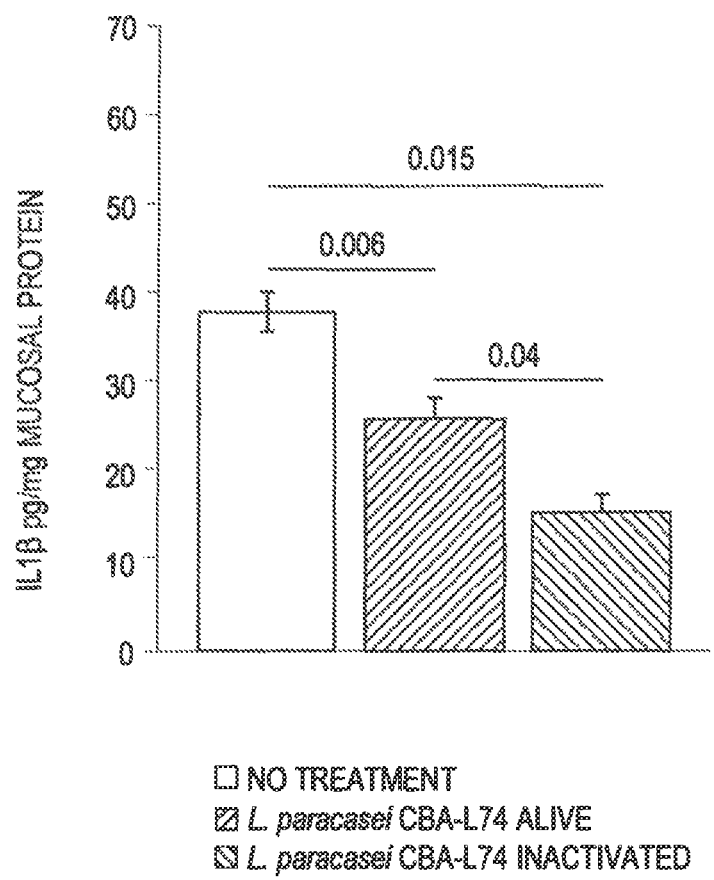
FIG. 4 is a graph depicting IL-1β production in intestinal mucosa of mice supplemented L. paracasei CBA L74.
Figure 5:
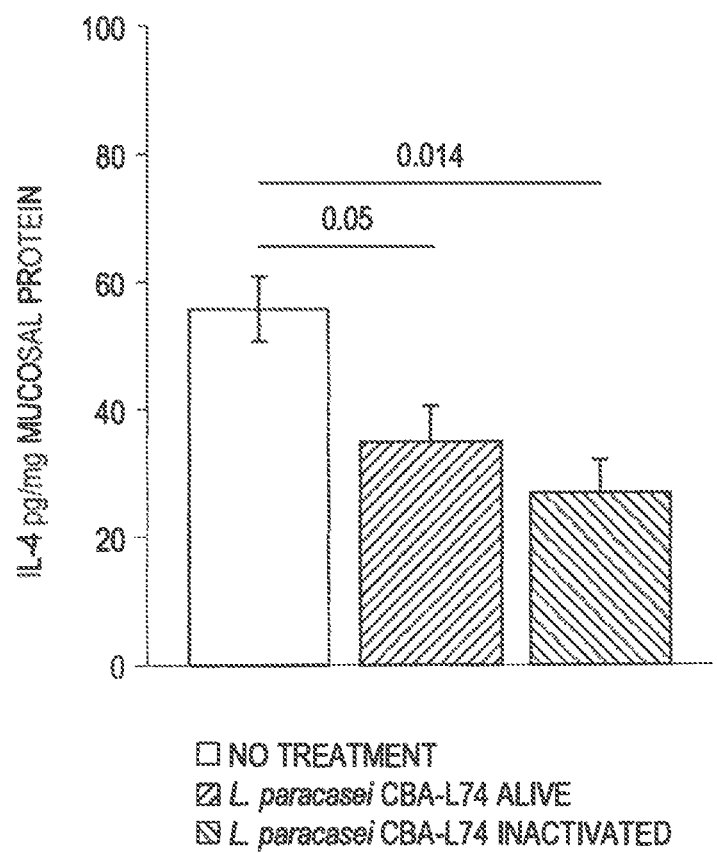
FIG. 5 is a graph depicting IL-4 production in intestinal mucosa of mice supplemented with L. paracasei CBA L74.
Figure 6:
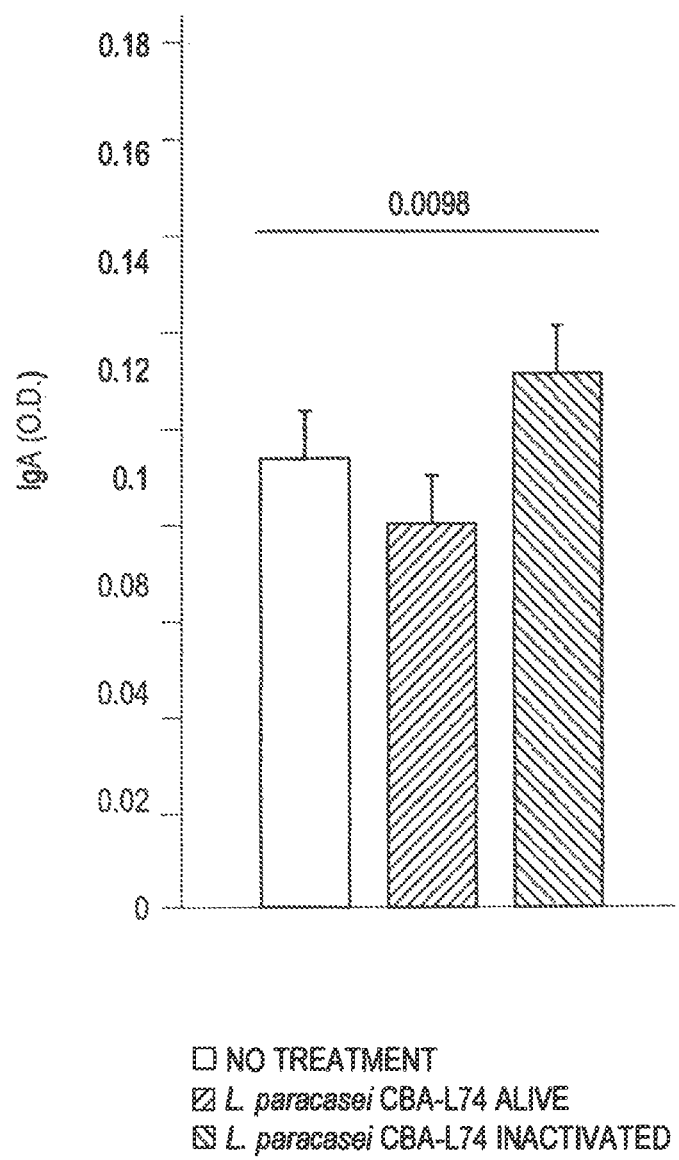
FIG. 6 is a graph depicting IgA production in intestinal mucosa of mice supplemented with L. paracasei CBA L74.

Cytokine and IgA expression: We then determined whether administration of *L. paracasei* CBA L74 (alive or inactivated) affected the level of anti- and proinflammatory cytokines in the intestinal mucosa. As shown in FIG. 4, the administration of *L. paracasei* CBA L74 alive or inactivated significantly decreased the level of IL-1β, a potent pro-inflammatory mediator, in the intestinal mucosa of mice. As shown in FIG. 5, we also observed a reduction in basal mucosal IL-4 level following administration of *L. paracasei* CBA L74 alive or inactivated. Finally, we determined the effect of different regimen supplementation on mucosal IgA level. Following two weeks of diet supplementation with *L. paracasei* CBA L74, animals were sacrificed and the intestinal mucosa collected and homogenized. Total IgA was then measured by ELISA and values normalized to total mucosal proteins. As shown in FIG. 6, heat killed *L. paracasei* CBA L74 significantly increased mucosal IgA.

Figure 7:
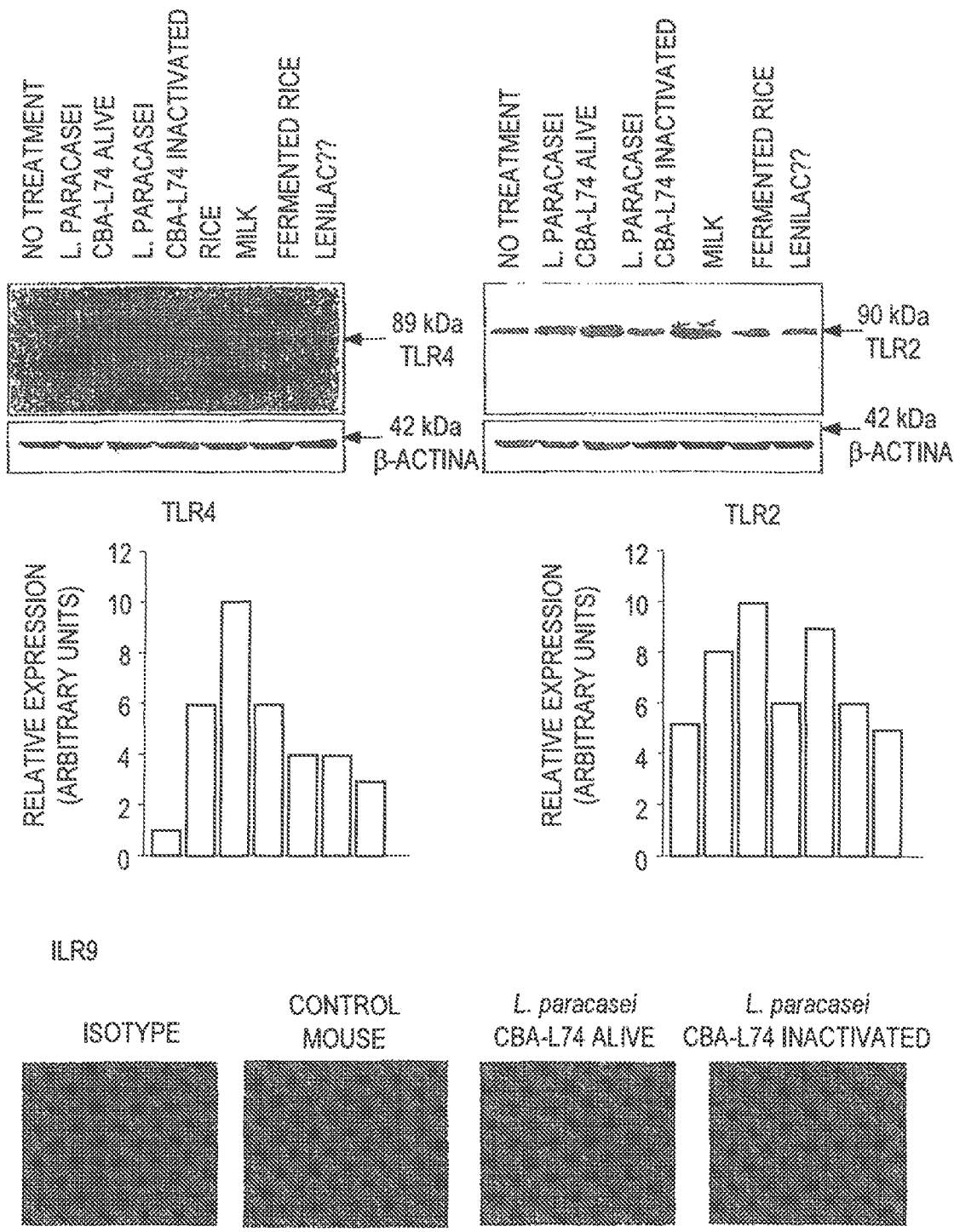
FIG. 7 depicts an analysis of levels of TLR2, TLR4 and TLR9 in intestinal mucosa of mice supplemented with L. paracasei CBA L74.
Figure 8:
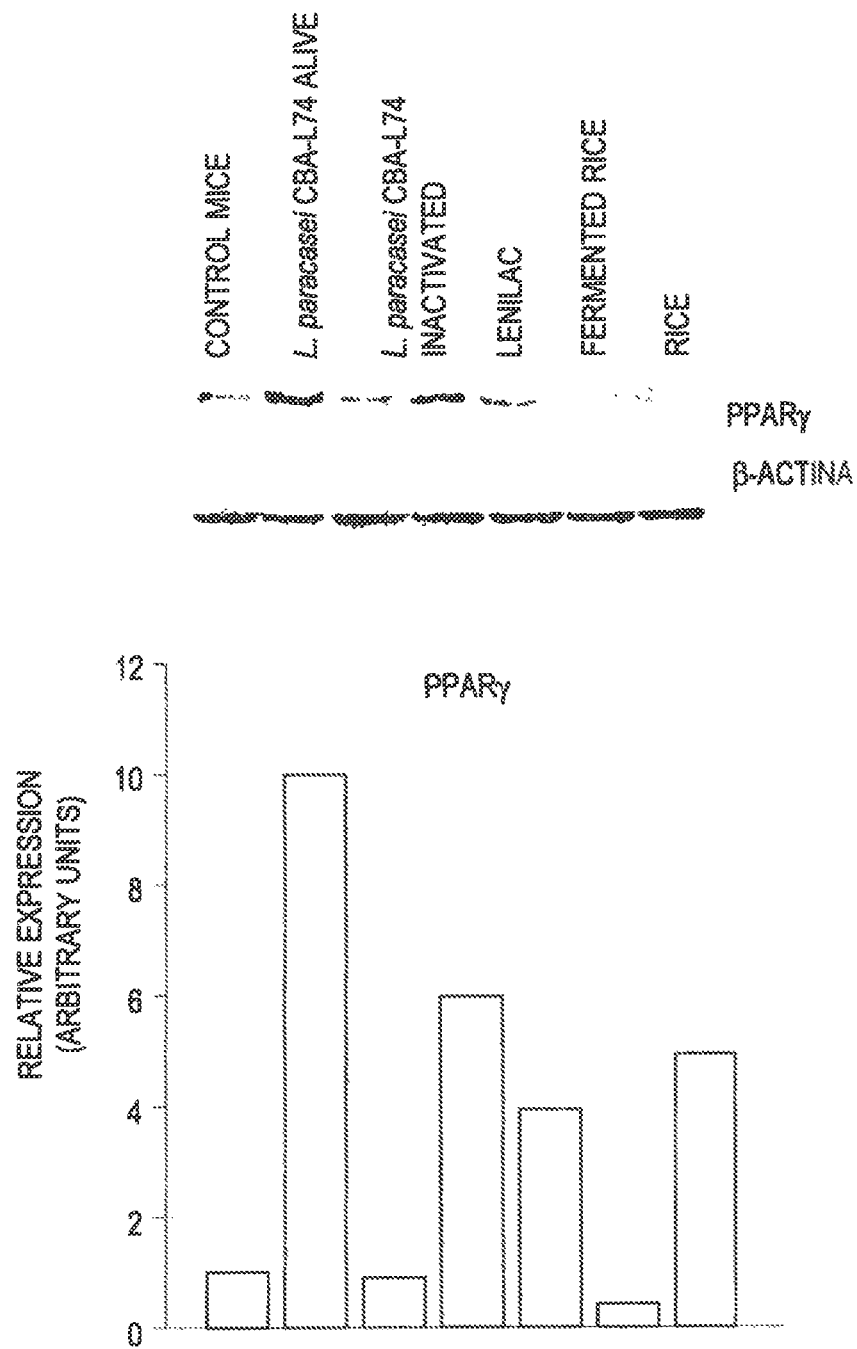
FIG. 8 depicts an analysis of levels of PPARγ in intestinal mucosa of mice supplemented with L. paracasei CBA L74.

Innate immunity: We analyzed the effect of dietary supplementation on levels of Toll-Like Receptor 2, 4 and 9. These receptors are involved in the recognition of conserved bacterial structures and thus play a key role in modulating the reactivity of immune and non-immune cells toward microbial conserved structures. As shown in FIG. 7, diet supplementation with *L. paracasei* CBA L74, live or heat inactivated, increased levels of protein expression of TLR2 and TLR4. We also assayed the effect of dietary supplementation on levels of PPARγ in the mucosa. As shown in FIG. 8, Live *L. paracasei* CBA L74 significantly increased the level of PPARγ.

Example 7: Effects of *L. paracasei* CBA L74 on Levels of Circulating Cytokines

Figure 9A:
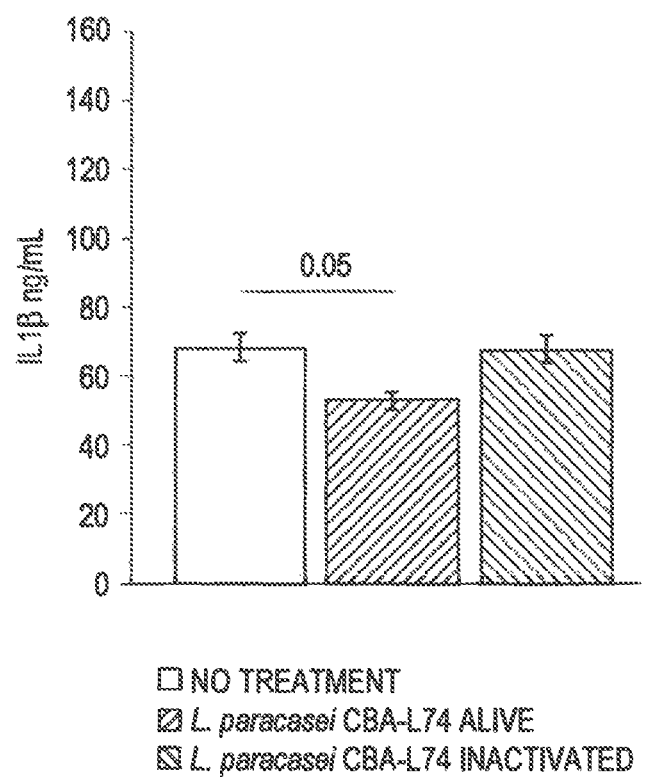
FIG. 9A is a graph depicting serum IL-1β levels in mice supplemented with L. paracasei CBA L74.
Figure 9B:
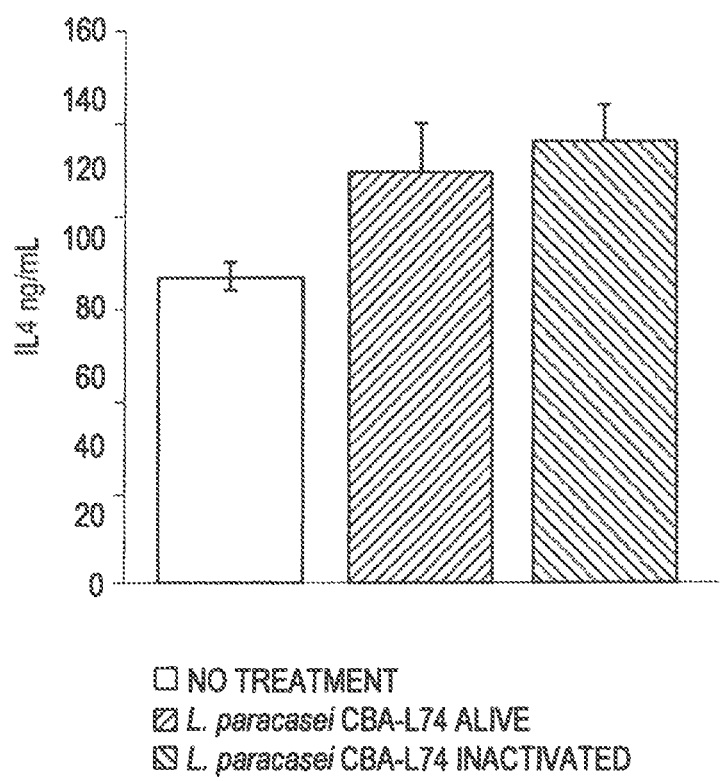
FIG. 9B is a graph depicting serum IL-4 levels in mice supplemented with L. paracasei CBA L74.

To assess whether the diet supplements were able to modify the level of circulating cytokines, we measured the effects of the dietary administration of the strain (alive or inactivated) on anti- and pro-inflammatory cytokines level in the serum. As shown in FIGS. 9A and 9B, Live *L. paracasei* CBA L74 induced a statistically significant decrease in IL-1β and a modest increase in circulating IL-4, respectively.

Example 8: Effects of *L. paracasei* CBA L74 on Dendritic Cell and T-Lymphocyte Activity We next focused on the impact of dietary supplementation with *L. paracasei* CBA L74 on immune cells relevant to the activity of mucosal-associated immune system, namely dendritic cells and lymphocytes. We evaluated the phenotype of DCs within the Peyers Patches (PP), since these cells are instrumental in establishing the fate of an antigen and contribute to the environment that will determine the nature of the adaptive immune response.

As shown in the Table in FIG. 10, *L. paracasei* CBA L74 supplementation (live or inactivated) decreased the expression of the co-stimulatory molecule CD80 and of the adhesion molecule CD40 whereas MHCII expression was up-regulated. These data suggested that the DCs from *L. paracasei* CBA L74 supplemented animals seemed less ready to interact with T-cells and to mount an immune response but their ability to process and present antigens was preserved.

We then determined the ability of diet supplementation with *L. paracasei* CBA L74 to modify the reactivity of DCs to pro-inflammatory stimuli (such as bacterial LPS and CpG). Exposure of DCs from control mice to LPS or CpG induced a strong up-regulation of CD80 in control DCs. Supplementation with heat inactivated *L. paracasei* CBA L74 DC did not modify the reactivity to inflammatory stimuli. Supplementation with live bacteria significantly reduced LPS- and CpG-induced CD80 up-regulation.

Figure 11A:
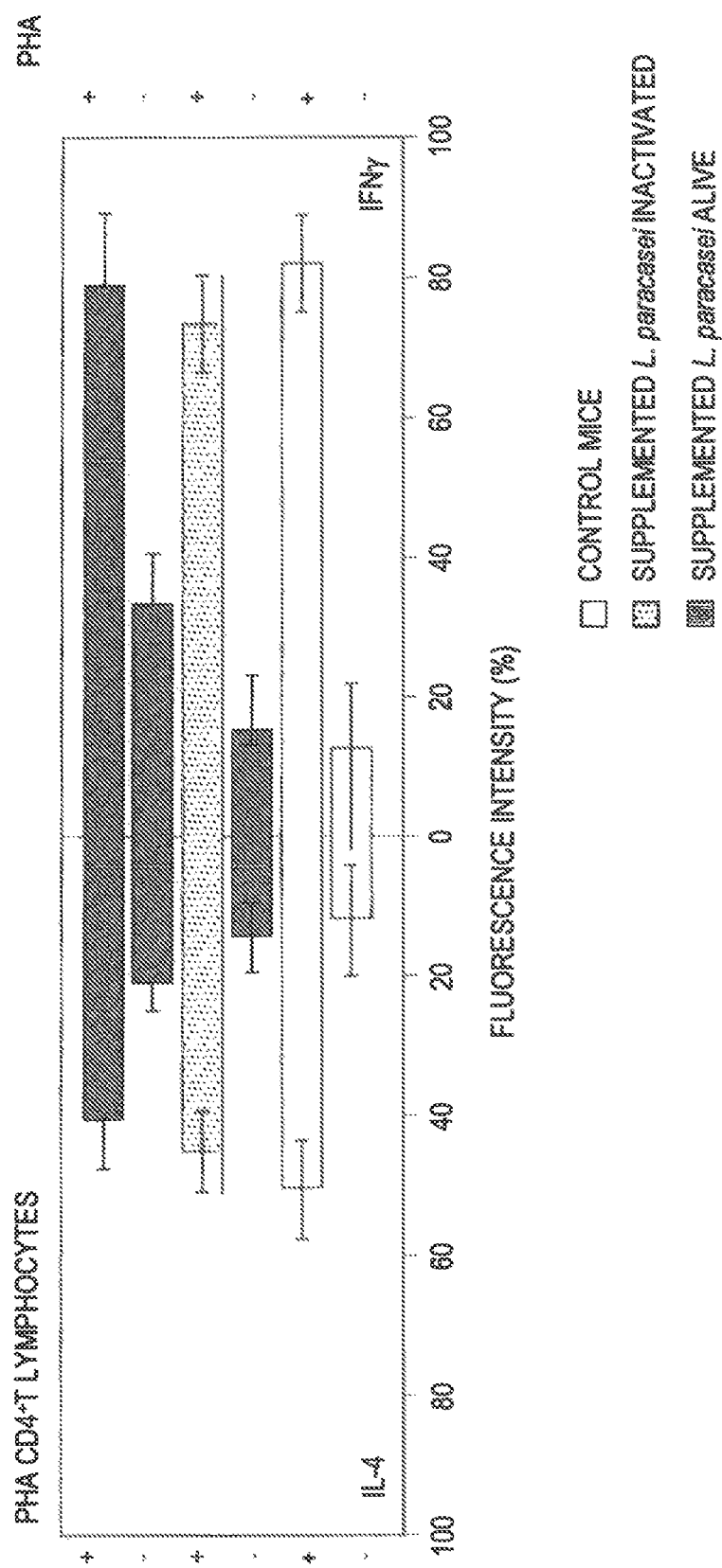
FIG. 11A is a graph depicting intestinal CD4+ lymphocyte phenotypes in mice supplemented with L. paracasei CBA L74.

Finally, we investigated whether dietary supplementation with *L. paracasei* CBA L74 (live or inactivated) affected intestinal T-lymphocytes (either CD4+ and CD8+) polarization toward a Th1 or Th2 phenotype. For these studies, Peyer's Patches were exposed to PHA, a strong, non-specific stimulus and then lymphocyte polarization was evaluated by intrakine staining for IL-4 and IFN-γ. As shown in FIG. 11A, in the absence of PHA (the "basal condition") in CD4+ lymphocytes, IL-4 and IFN were almost in equilibrium.

Figure 11B:
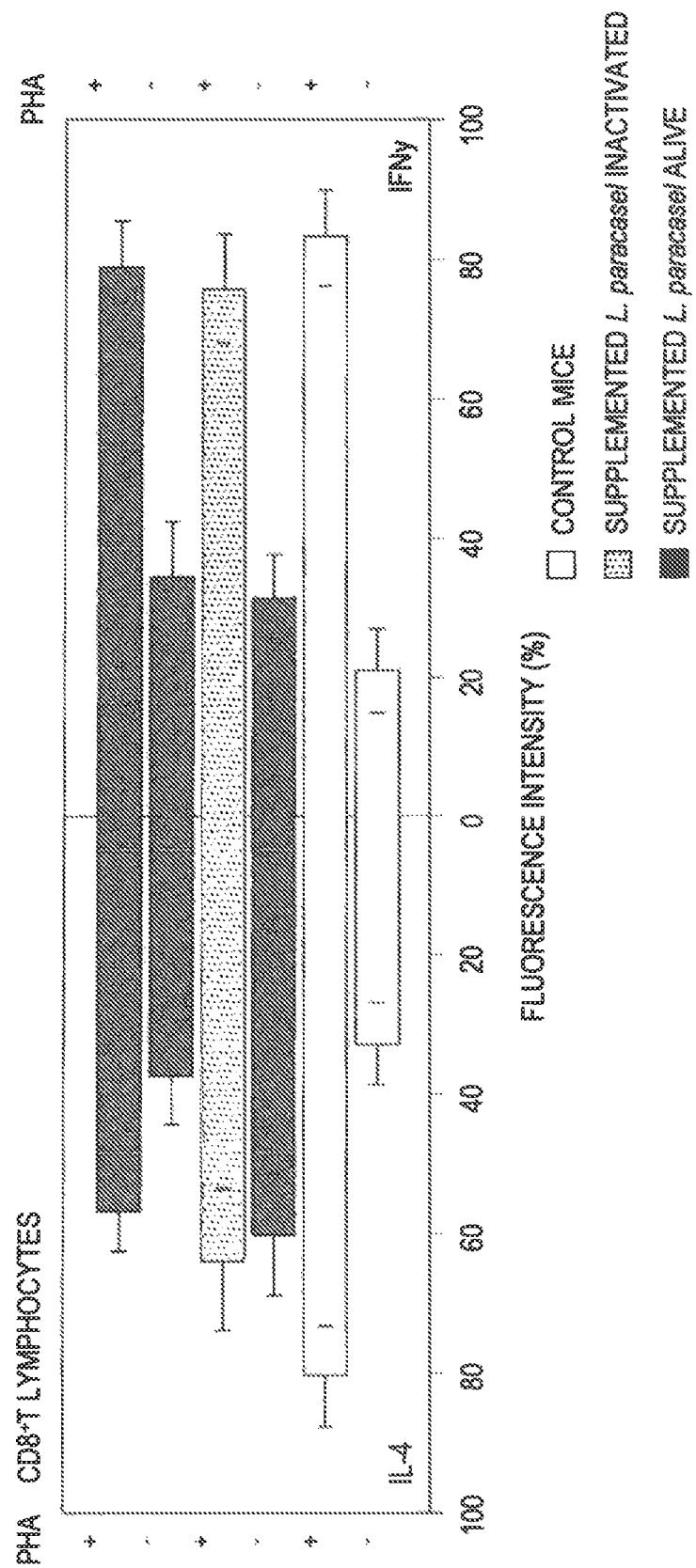
FIG. 11B is a graph depicting intestinal CD8+ lymphocyte phenotypes in mice supplemented with L. paracasei CBA L74.

About 10-12% of the cells were positive for these cytokines. As shown in FIG. 11B, for CD8+ lymphocytes in the basal condition, there was a slight predominance of IL-4 over IFN expressing cells. Exposure of either CD4+ or CD8+ lymphocytes to PHA caused a strong increase in intracellular staining for IL-4 and IFN-γ with bias toward IFN-γ production.

In CD4+ cells, dietary supplementation with live *L. paracasei* CBA L74 increased IFN-γ levels in the basal condition. Following PHA exposure there were no significant differences in the response among the supplemented groups (FIG. 11A). In CD8+ lymphocytes, oral supplementation with inactivated *L. paracasei* CBA L74 favored a Th2 profile with a stimulation of IL-4 production over IFN-γ production (FIG. 11B) The anti-inflammatory profile is further supported by the blunted response to PHA. A similar trend was evident also in CD8+ lymphocytes isolated from mice supplemented with live *L. paracasei* CBA-L74, although less pronounced.

Example 9: Effect of Milk Fermented by *L. paracasei* CBA L74 on Immune System Markers in the Intestinal Mucosa Mice were supplemented twice a day for two weeks with either: 1) Control (PBS); 2) Skim milk (not fermented); 3) Skim milk fermented with *L. paracasei* CBA L74 ($1\times10^8$ cfu/ml), 4) Skim milk fermented with *S. thermophilus* ($6.7\times10^6$ cfu/ml); 5) Skim milk fermented with *L. paracasei* CBA L74 ($1\times10^8$ cfu/ml) and *S. thermophilus* ($1.18\times10^7$ cfu/ml), 6) Skim milk fermented with *L. paracasei* CBA L74 ($1.9\times10^9$ cfu/die) and *S. thermophilus* ($2.2\times10^8$ cfu/ml). At the end of the treatment animals were sacrificed and intestinal mucosa and Peyer's Patches were collected and processed for analysis as described below.

Figure 12:
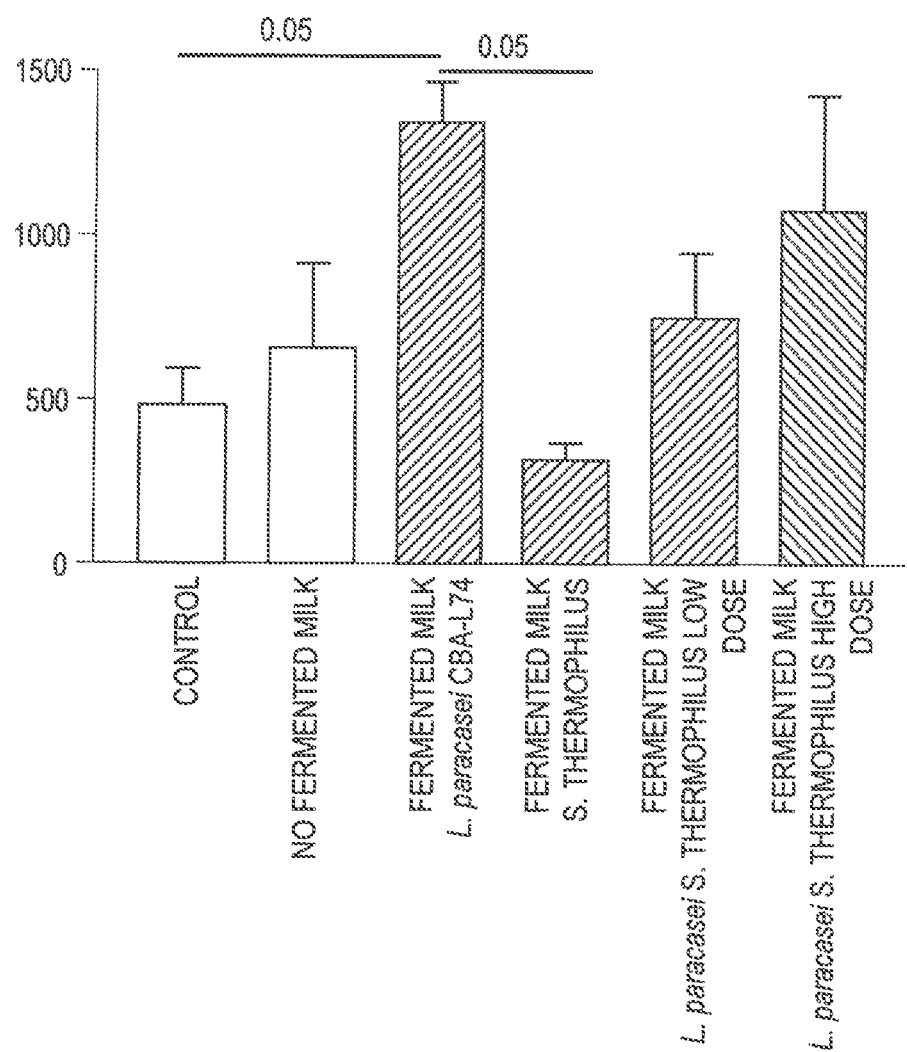
FIG. 12 is a graph depicting IL-10 production in intestinal mucosa of mice supplemented with milk fermented by L. paracasei CBA L74.
Figure 13:
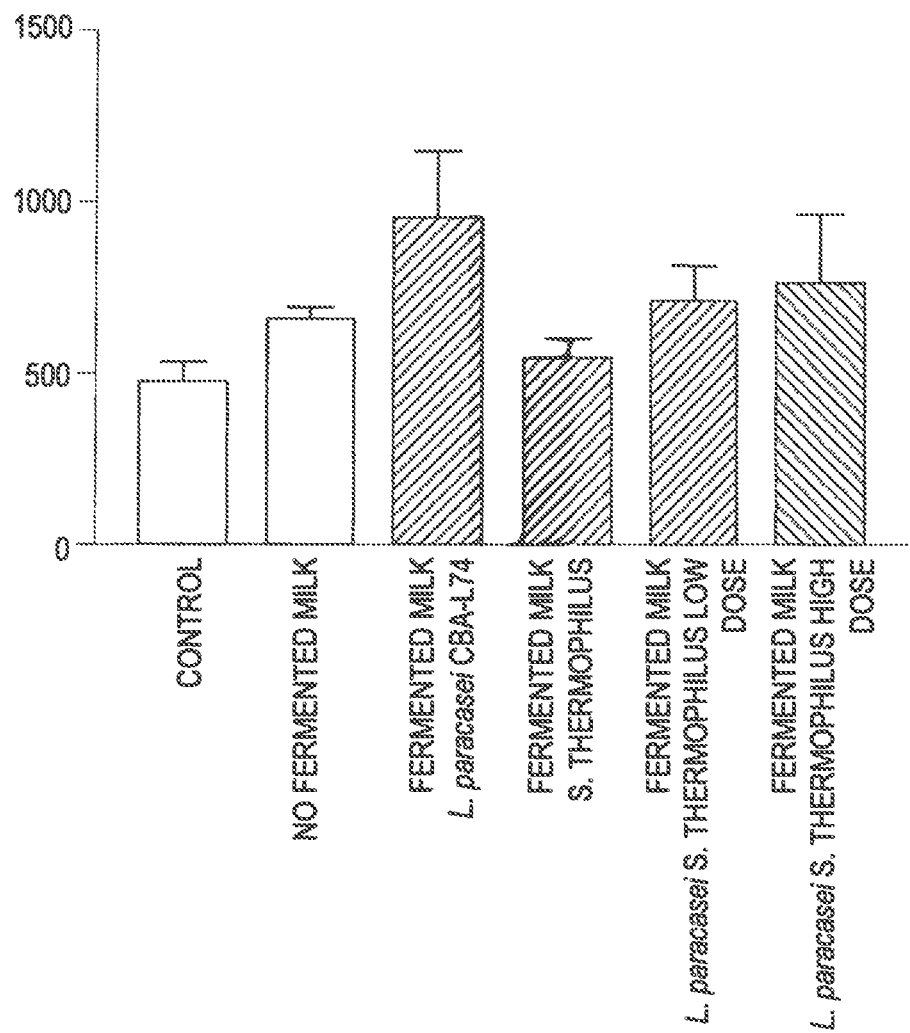
FIG. 13 is a graph depicting IL-1β production in intestinal mucosa of mice supplemented with milk fermented by L. paracasei CBA L74.

Levels of cytokines in the intestinal mucosa. As shown in FIG. 12, supplementation with skim milk fermented with *L. paracasei* CBA L74 caused a significant increase IL-10 levels in the intestinal mucosa. Administration of skim milk fermented with *S. thermophilus* induced a slight reduction as compared to controls. Administration of milk fermented with both strains at higher dosage induced a 2.1-fold increase in mucosal IL-10. None of the treatments had any significant effect on mucosal IL-1β although supplementation with skim milk fermented with *L. paracasei* CBA L74 caused a slight increase in mucosal levels of this cytokine.

Myeloperoxidase activity in the intestinal mucosa. Myeloperoxidase (MPO) activity was assayed in intestinal mucosa homogenates. Administration of non fermented or fermented milk with different bacteria did not induce statistically significant differences in the myeloperoxidase activity, although there was a slight increase in MPO activity observed in the mucosa of animals receiving non fermented milk.

Figure 14:
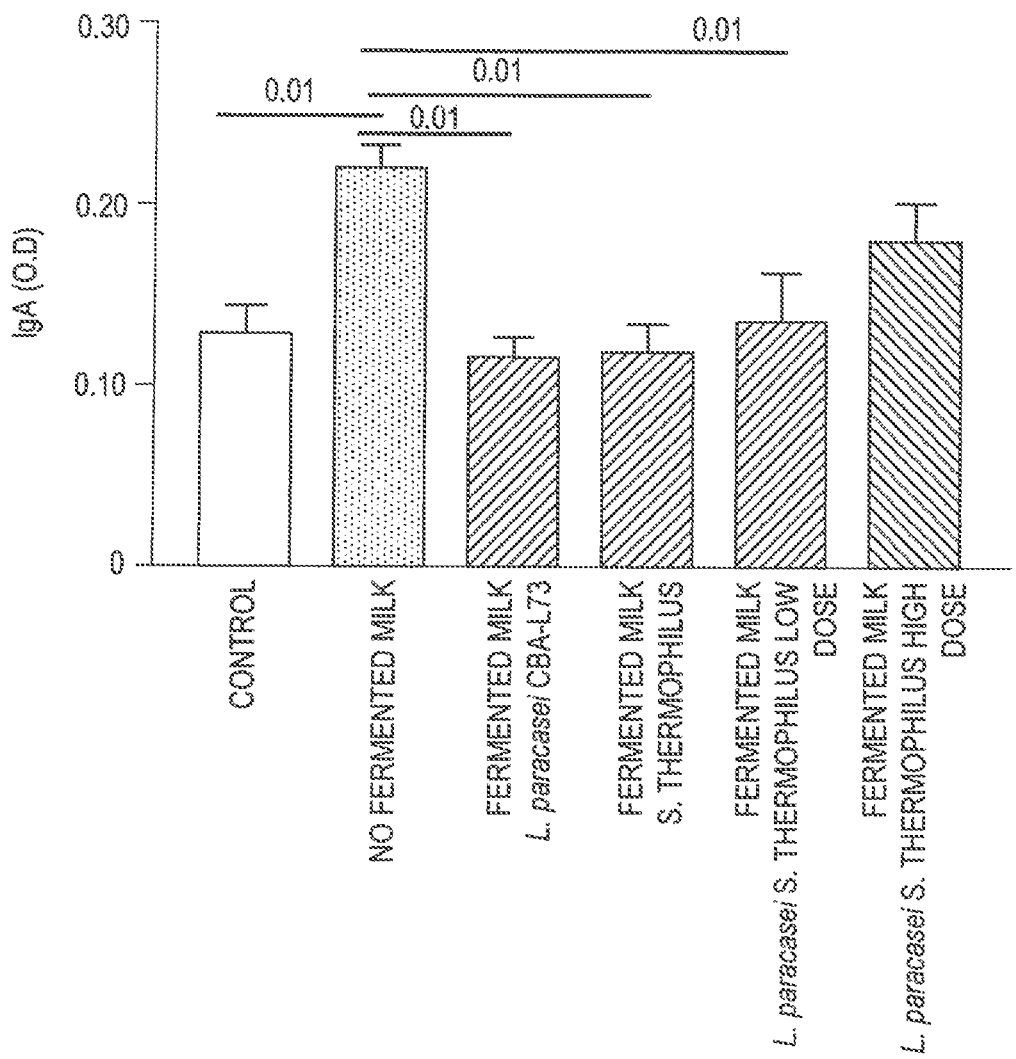
FIG. 14 is a graph depicting IgA production in intestinal mucosa of mice supplemented with milk fermented by L. paracasei CBA L74.

Levels of IgA in the intestinal mucosa. As shown in FIG. 14, supplementation with non-fermented skim milk caused a significant increase in the intestinal mucosa IgA. This increase was not observed in animals supplemented with skim milk fermented with either *L. paracasei* CBA L74 or *S. thermophilus* alone. Administration of milk fermented with both strains at higher dosage induced an increase in mucosal IgA.

Figure 15A:
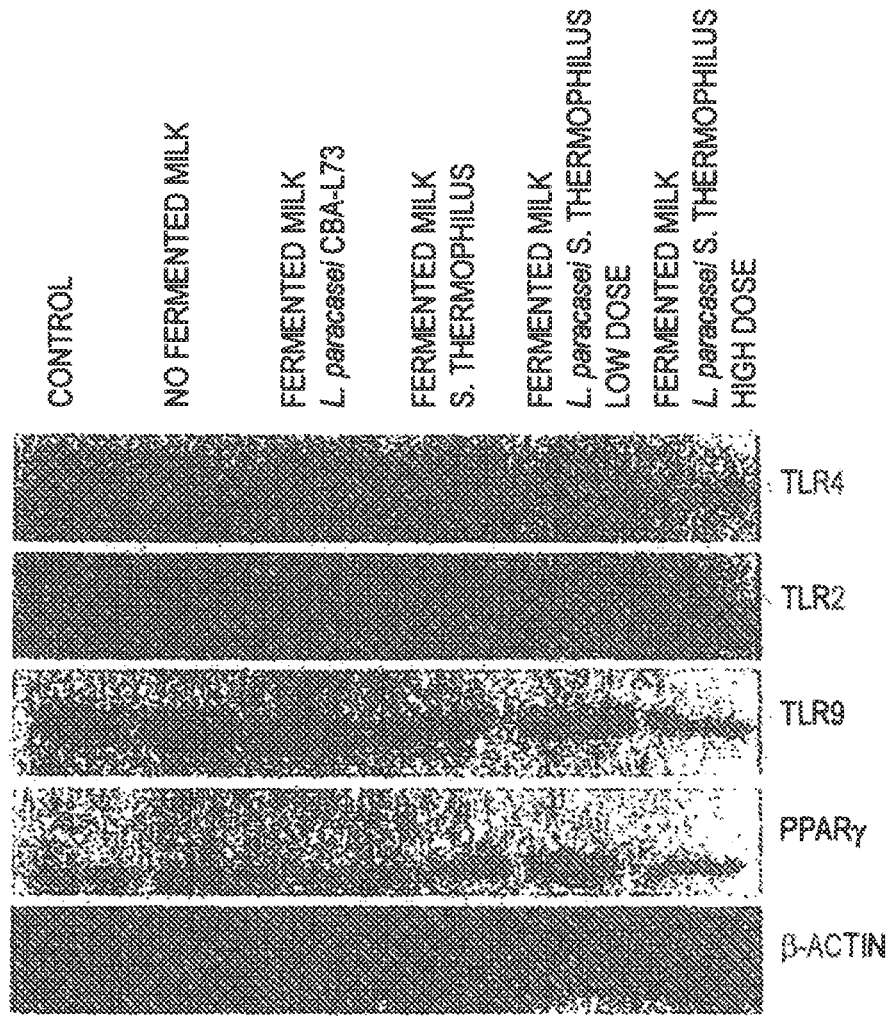
FIG. 15A and FIG. 15B each depict an analysis of levels of TLR2, TLR4, TLR9 and PPARγ in intestinal mucosa of mice supplemented with milk fermented by L. paracasei CBA L74.
Figure 15B:
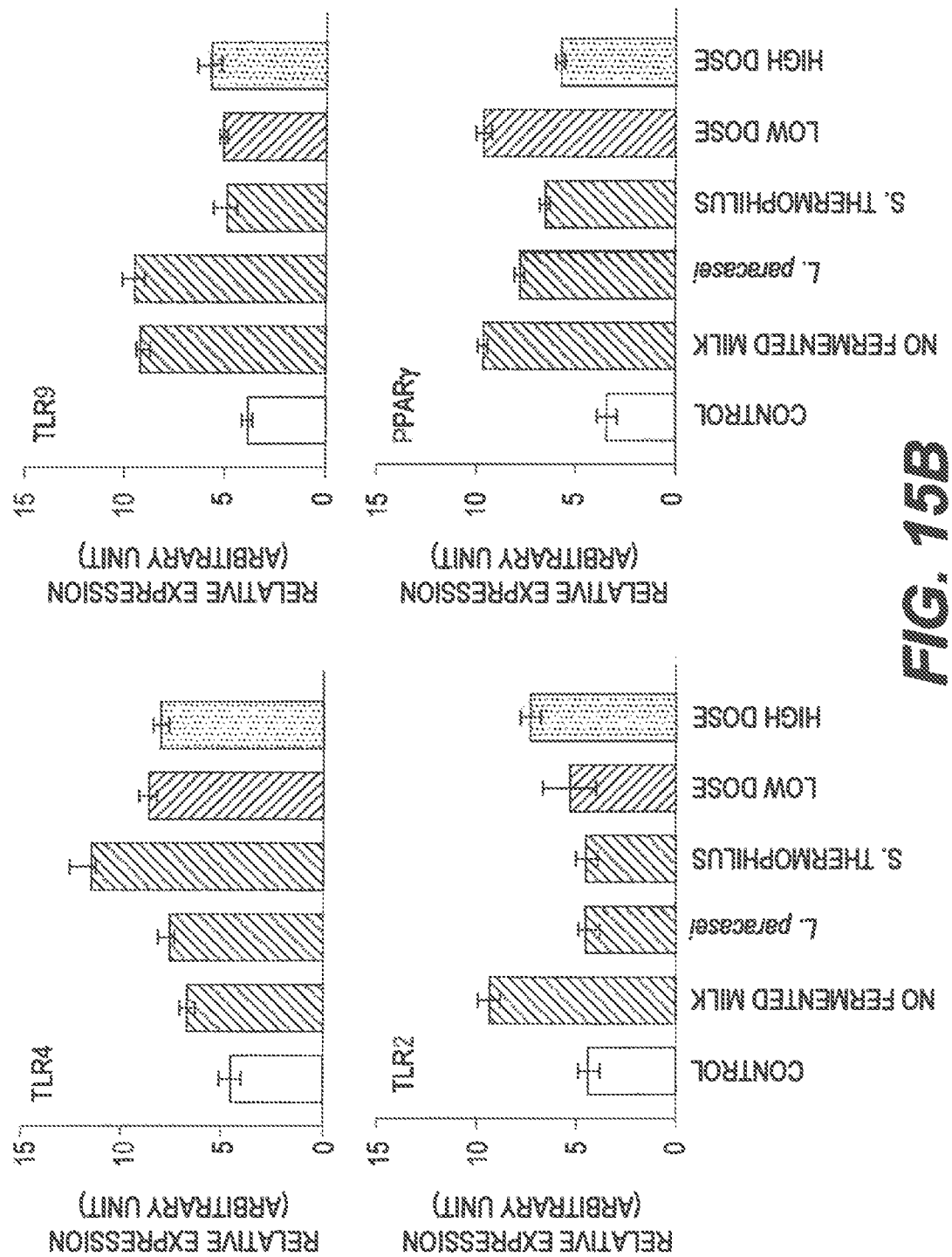

Levels of TLR2, TLR4, TLR9 and PPARγ in the intestinal mucosa. We next determined by WB the mucosal levels of key receptors of innate immune system. As shown in FIGS. 15A and 15B, none of the treatments had any significant effect on TLR4 receptor expression. Non-fermented milk caused a modest increase in TLR2. Administration of skim milk fermented with either *L. paracasei* CBA L74 or *S. thermophilus* alone or in combination at the lower dose prevented this effect. A modest increase, comparable to milk alone, in TLR2 was also evident in mice receiving milk fermented with both strains at higher dosage. Administration of skim milk alone had profound effects on TLR9 levels, whereas administration of fermented milk with both strains re-established mucosal levels comparable to controls. As shown in FIGS. 15A and 15B, administration of non-fermented milk per se caused a strong increase in mucosal PPARγ. A similar effect was evident in mice supplemented with skim milk fermented with *L. paracasei* CBA L74 and the lower dose of milk fermented with both strains.

Figure 16:
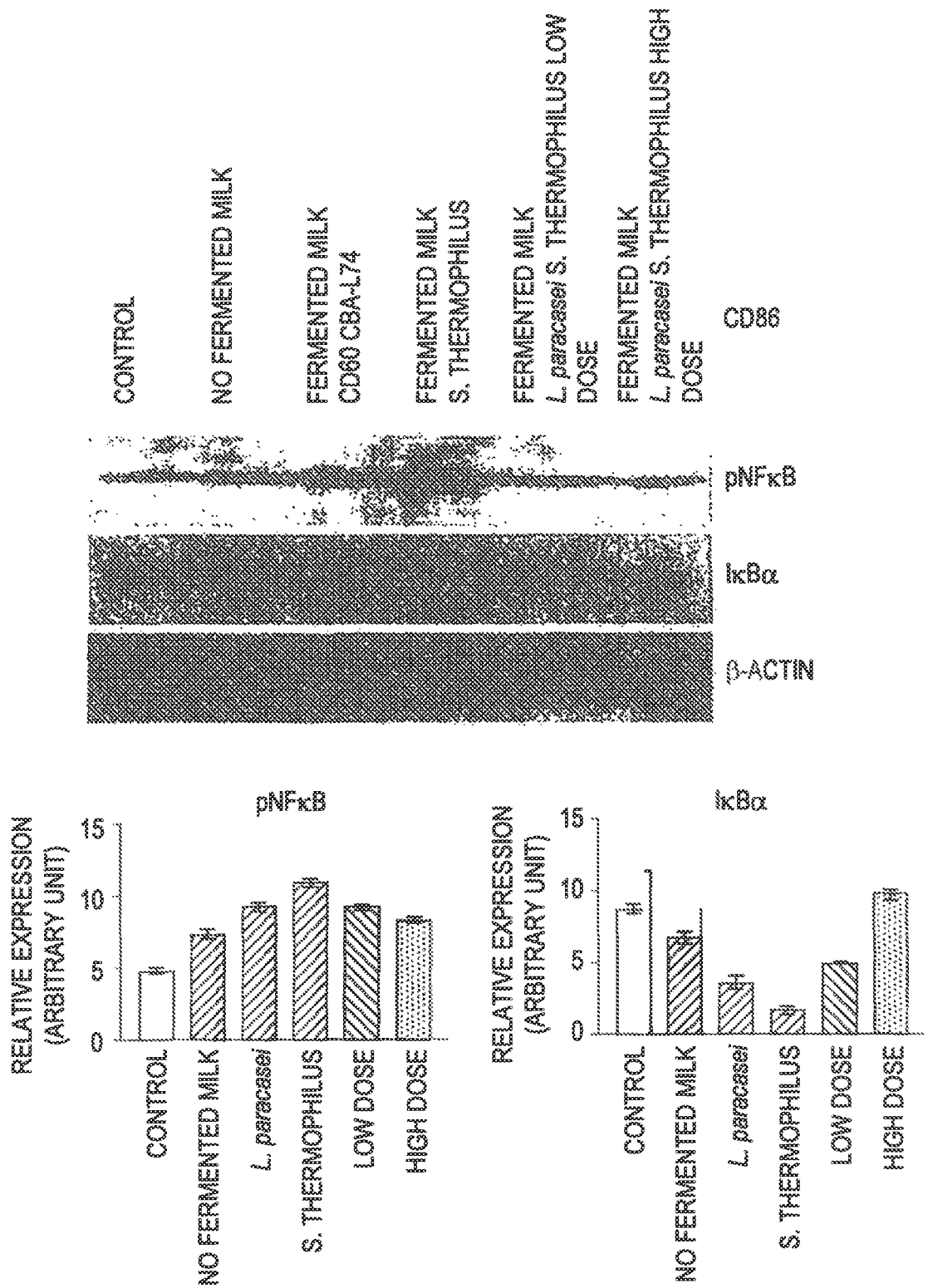
FIG. 16 depicts an analysis of levels of pNF-kB and IKBα in intestinal mucosa of mice supplemented with milk fermented by L. paracasei CBA.

Levels of pNF-kB and IKB in the intestinal mucosa. We determined the activation status of NF-κB, a key transcription factor involved in both intestinal inflammation and epithelial cell survival. As shown in FIG. 16, activated NF-KB (pNF-κB) was detectable in the control, normal mucosa. Following the different treatments, we observed only a slight increase in pNF-κB levels in the mucosa of mice treated with skim milk fermented with either *L. paracasei* CBA L74 or *S. thermophilus* alone, whereas in mice receiving skim milk fermented with both strains, pNF-κB was comparable to controls. The increase in pNF-κB paralleled the disappearance of the inhibitory subunit of NF-κB, IKB, that was not detectable in the mucosa of mice supplemented with skim milk fermented with either *L. paracasei* CBA L74 or *S. thermophilus* alone. Mice receiving skim milk fermented with both strains showed IkB levels comparable to controls.

Figure 17:
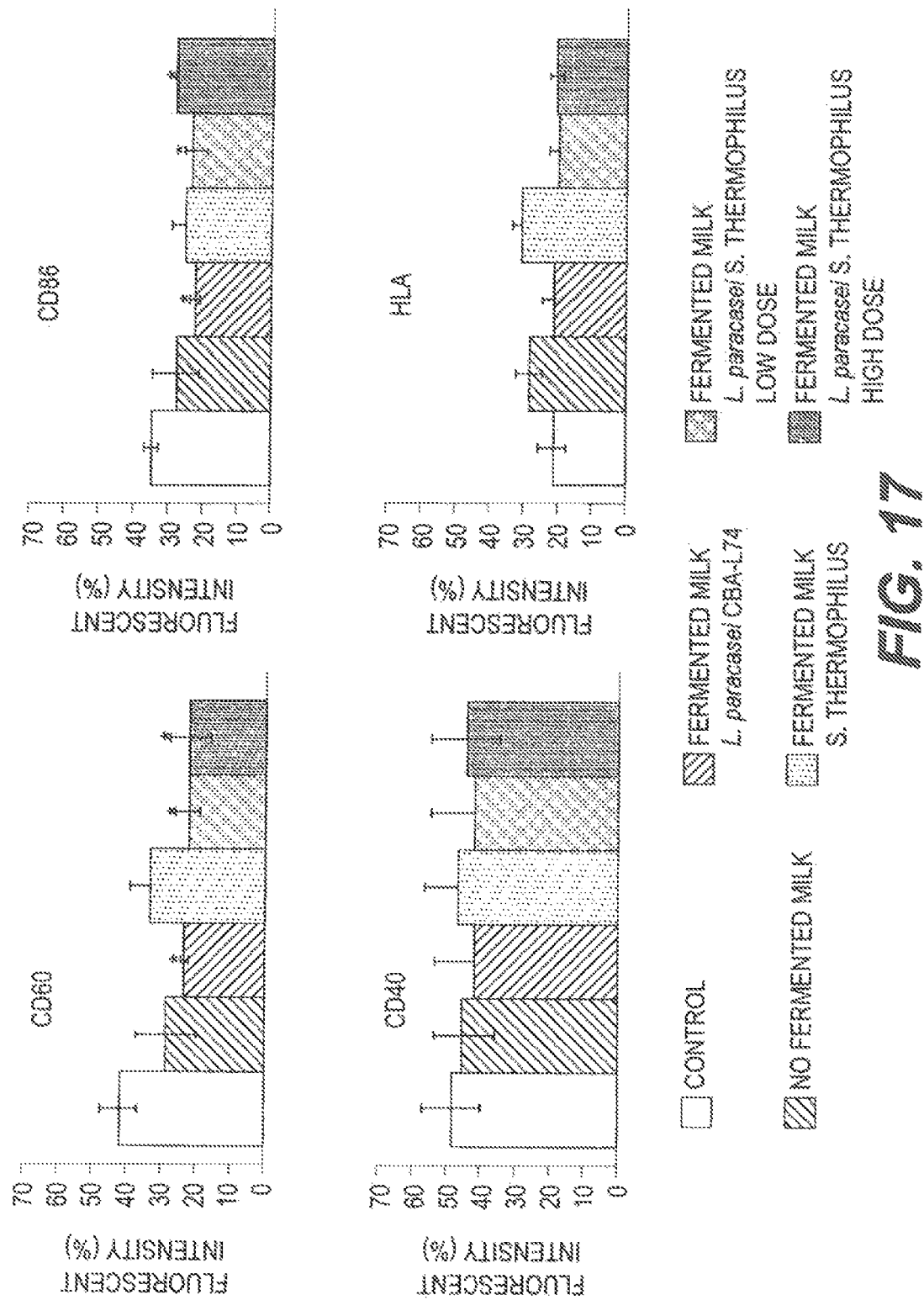
FIG. 17 depicts an analysis of the effect of L. paracasei CBA L74 on DC cell phenotype in mice supplemented with milk fermented by L. paracasei CBA.

Example 10: Effect of Milk Fermented by *L. paracasei* CBA L74 on Dendritic Cell Phenotype in the Intestinal Mucosa Phenotype of dendritic cells extracted from Peyer's Patches. We examined the effect of diet supplementation on the phenotype of intestinal DCs. The results of this analysis are shown in FIG. 17. Administration of milk fermented with *L. paracasei* alone as well as with *L. paracasei* and *S. thermophilus* at lower and higher doses produced a statistically significant decrease in CD80 and CD86 expression as compared to control mice (* means p<0.05 vs control), whereas HLAII and CD40 levels overall remained stable. Data in FIG. 17 are expressed as mean±S.E. of three separate experiments.

Figure 18:
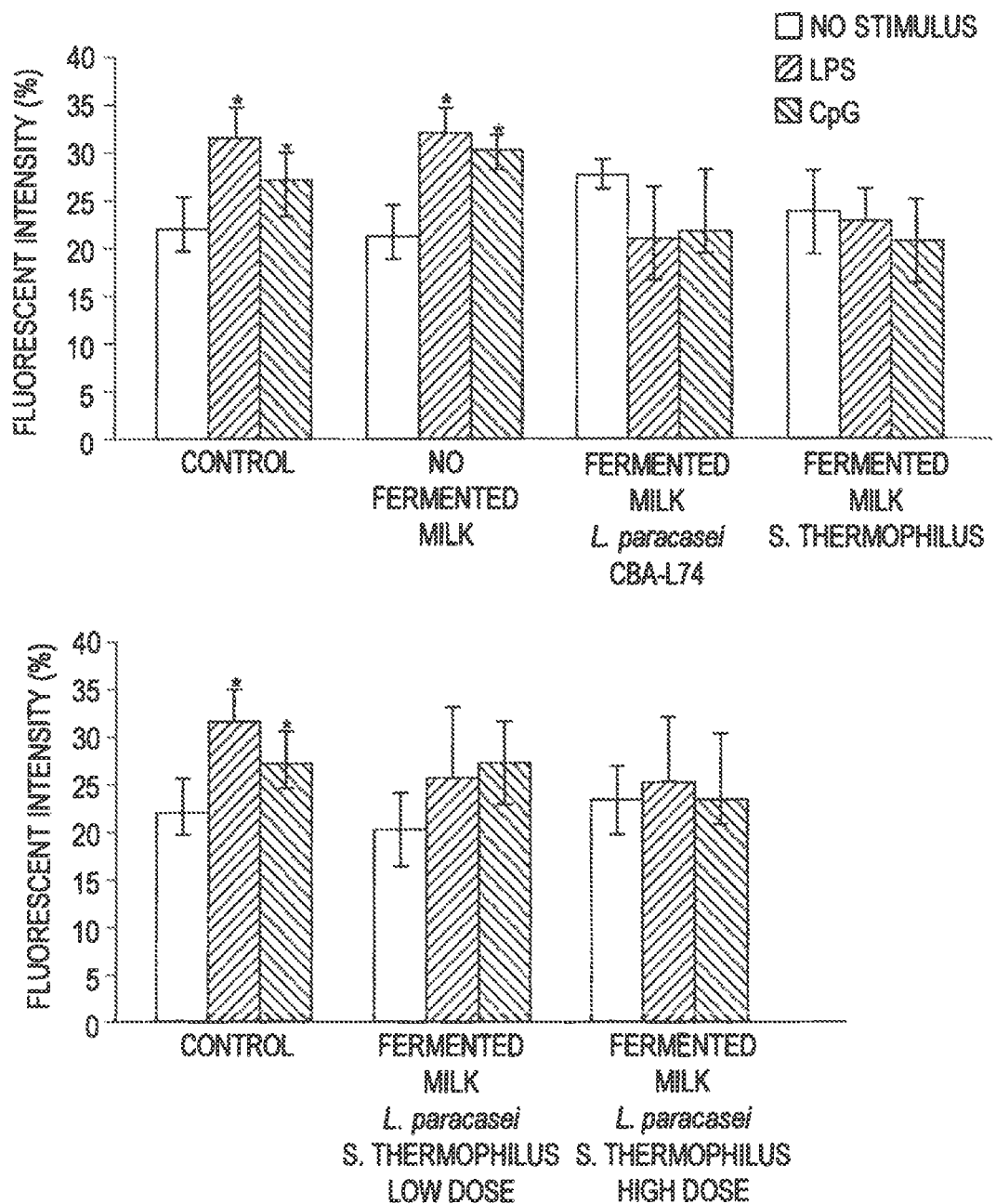
FIG. 18 is an analysis of the effect of L. paracasei CBA L74 on DC cell phenotype after exposure to LPS or CpG in mice supplemented with milk fermented by L. paracasei CBA.

Responses of dendritic cells exposed to LPS/CpG. We determined the ability of diet supplementation to modify the reactivity of DCs to pro-inflammatory stimuli (such as bacterial LPS and CpG). As shown in FIG. 18, exposure of isolated DCs isolated from control animals to LPS and CpG caused a significant increase in the expression of CD80 (* means p<0.05 vs un-stimulated DCs from control mice). A similar effect was observed in DCs purified from mice receiving non-fermented milk (° means p<0.05 vs un-stimulated DCs from mice treated with non-fermented milk). Administration of skim milk fermented with *L. paracasei* CBA L74 alone completely prevented LPS-mediated effects in mice treated with non-fermented milk, although it was less effective on CpG-induced CD80 upregulation. Skim milk fermented with *S. thermophilus* alone prevented LPS and CpG effects and reduced CD80 expression. Finally, administration of skim milk fermented with both strains prevented LPS- and CpG-induced CD80 up-regulation and maintained CD80 expression at basal levels. Data in FIG. 18 are expressed as mean±S.E. of three separate experiments.

Example 11: Effect of Milk Fermented by *L. paracasei* CBA L74 on T-Lymphocyte Phenotype in the Intestinal Mucosa Responses of intestinal lymphocytes CD4+ e CD8+ exposed to PHA. We asked whether dietary supplementation with milk (either fermented or unfermented) would affect intestinal T-lymphocytes (CD4+ and CD8+) polarization toward a Th1 or Th2 phenotype. Peyer's Patches derived lymphocytes were exposed to PHA, and then lymphocyte polarization was evaluated by staining for intracellular IL-4 and IFN-γ.

Figure 19:
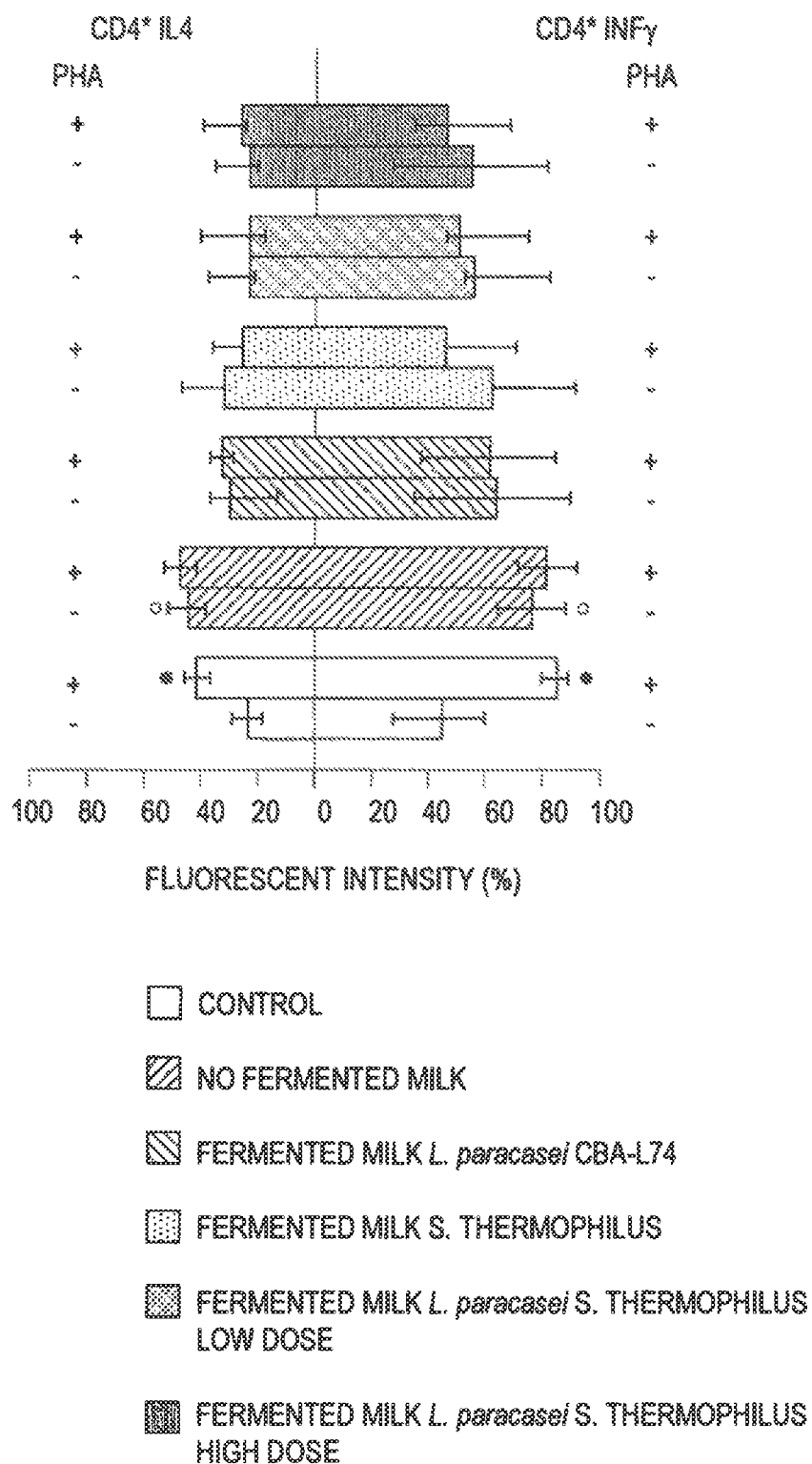
FIG. 19 is a graph depicting intestinal CD4+ lymphocyte phenotypes in mice supplemented with milk fermented by L. paracasei CBA L74.

As shown in FIG. 19, exposure to PHA significantly increased IL4 and IFNγ production in CD4+ lymphocytes from control mice (° means p<0.05 vs unstimulated lymphocytes from control mice). This induction was not observed in mice treated with either non-fermented or fermented milk. Following supplementation with non-fermented milk, CD4+ lymphocytes showed increased basal levels of IL4 and IFN-γ as compared to control animals (° means p<0.05 vs un-stimulated lymphocytes from control mice). These data suggested that supplementation with fermented milk prevented non-specific activation and maintained IL4 and IFN-γ production at basal levels.

Figure 20:
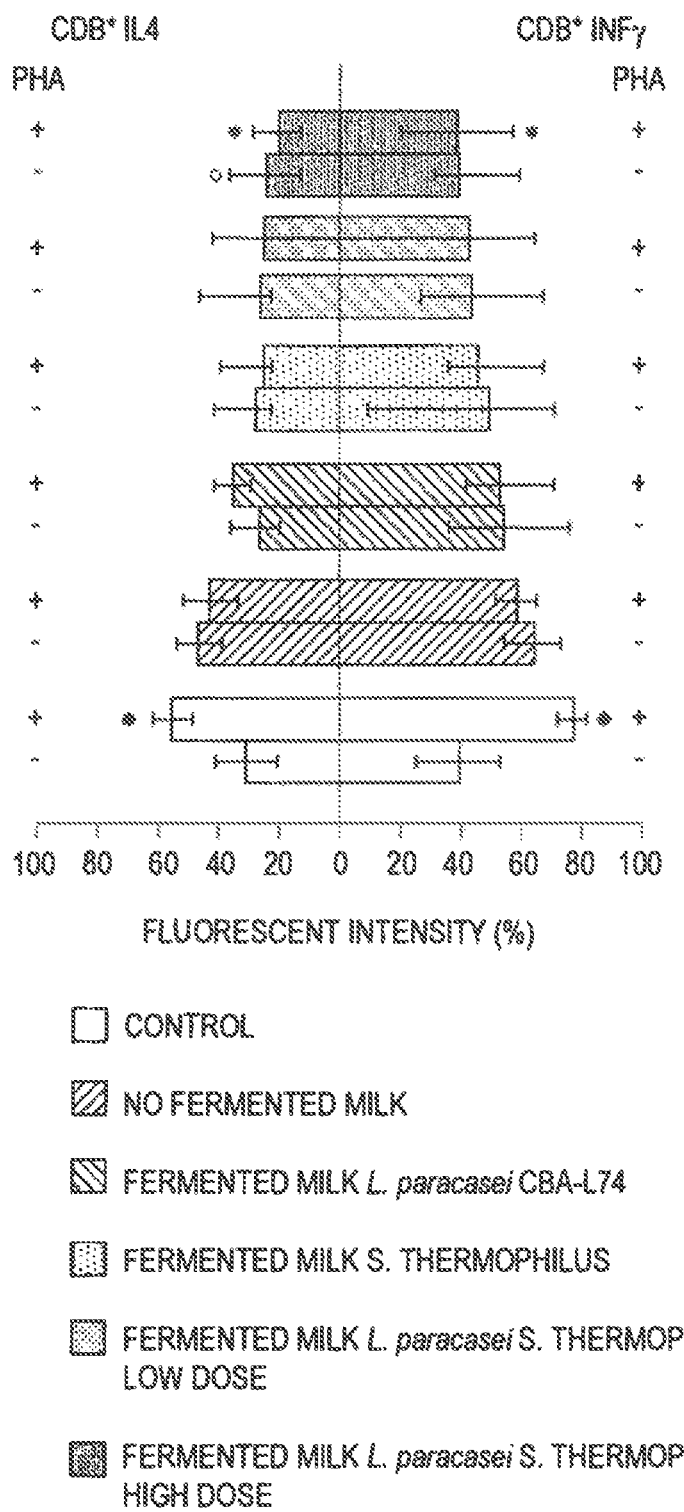
FIG. 20 is a graph depicting intestinal CD8+ lymphocyte phenotypes in mice supplemented with milk fermented by L. paracasei CBA L74.

As shown in FIG. 20, exposure to PHA in CD8+intestinal lymphocytes from control mice increased production of IL4 and IFNγ (* means p<0.05 vs non-stimulated lymphocytes from control mice). This induction was not observed in mice treated with either non-fermented or fermented milk. Administration of milk fermented with *L. paracasei* and *S. thermophilus* at higher dose decreased the basal production of IL4 whereas following stimulation with PHA, the levels of both IL4 and IFNγ were reduced as compared to stimulated lymphocytes from control mice (§ means p<0.05).

Figure 21:
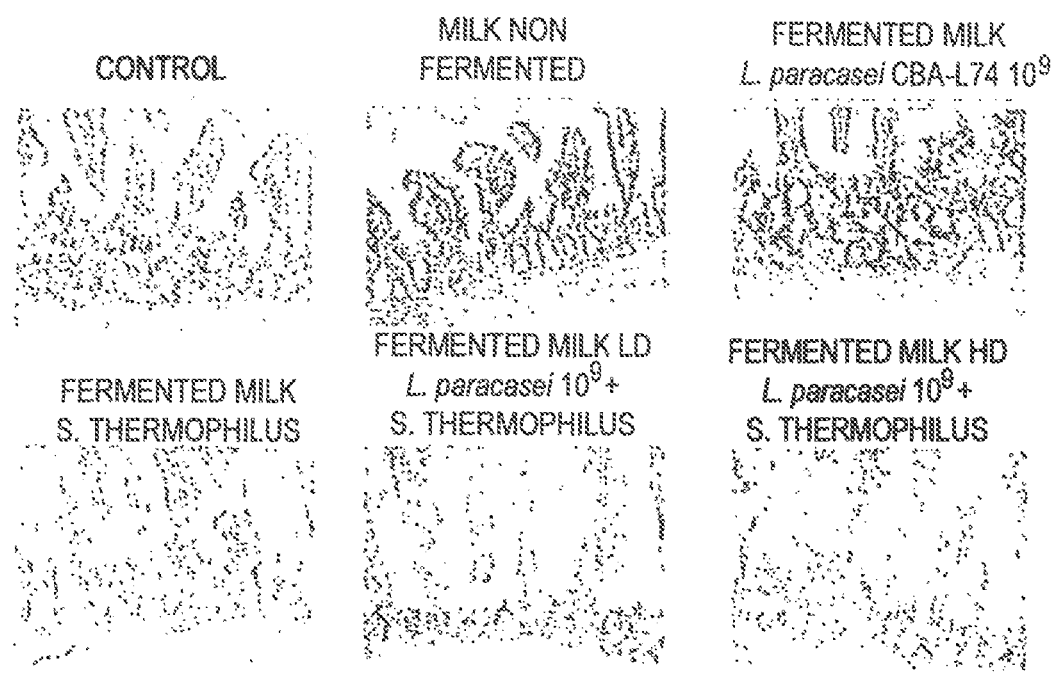
FIG. 21 shows histological evaluation of ileal mucosa in mice supplemented with milk fermented by L. paracasei CBA L74.

Example 12: Effect of Milk Fermented by *L. paracasei* CBA L74 on Intestinal Mucosa Histology To determine the distribution of proliferating cells in the intestinal mucosa, we performed an immunohistochemical analysis of expression of Ki67, an antigen expressed by dividing cells. In control mice there was a clear immunoreactivity in the intestinal crypts, whereas there was no staining on the villi. In the tissue from mice receiving non-fermented milk there was a stronger expression in the crypts, although there was no ectopic expression of the antigen. In mice receiving the different kind of fermented milk we observed comparable staining patterns. We have performed a histological evaluation of ileal mucosa of the different experimental groups. Results of this study are shown in FIG. 21. Administration of non-fermented milk reduced the number and length of intestinal villi, whereas the intestinal morphology was preserved in the animals receiving the various forms of fermented milk.

Example 13: Effect of Rice Fermented by *L. paracasei* CBA L74 on Immune System Markers in the Intestinal Mucosa These experiments were designed to evaluate the immuno-modulatory properties of *L. paracasei* CBA-L74-fermented cereals. Studies included daily intragastric administration for two weeks of: 1) Non fermented rice; 2) Fermented rice (with *L. paracasei* CBA L74) 100 mg day (corresponding to $2 \times 10^8$ cfu/L of *L. paracasei* CBA-L74) and 3) Fermented rice (with *L. paracasei* CBA L74) 500 mg day (corresponding to $10^9$ cfu/L of *L. paracasei* CBA-L74) Mice during the treatment period did not show any sign of illnesses or diarrhea. At the end of the treatment mice were killed and the Peyer's patches (PP) were collected aseptically. Epithelial cells were removed from PP by incubation in HBSS with no $Ca_2+$ plus EDTA and then tissues were subjected to enzymatic digestion. The single cell suspension was washed, resuspended in cold RMPI and used for the following tests.

We initially examined the effect of different diet supplements on the whole intestinal mucosa. First, we performed haematoxylin and eosin staining of paraffin embedded ileal sections. None of the diet supplements used had significant effects on intestinal architecture or caused an infiltrate of inflammatory cells.

Figure 22:
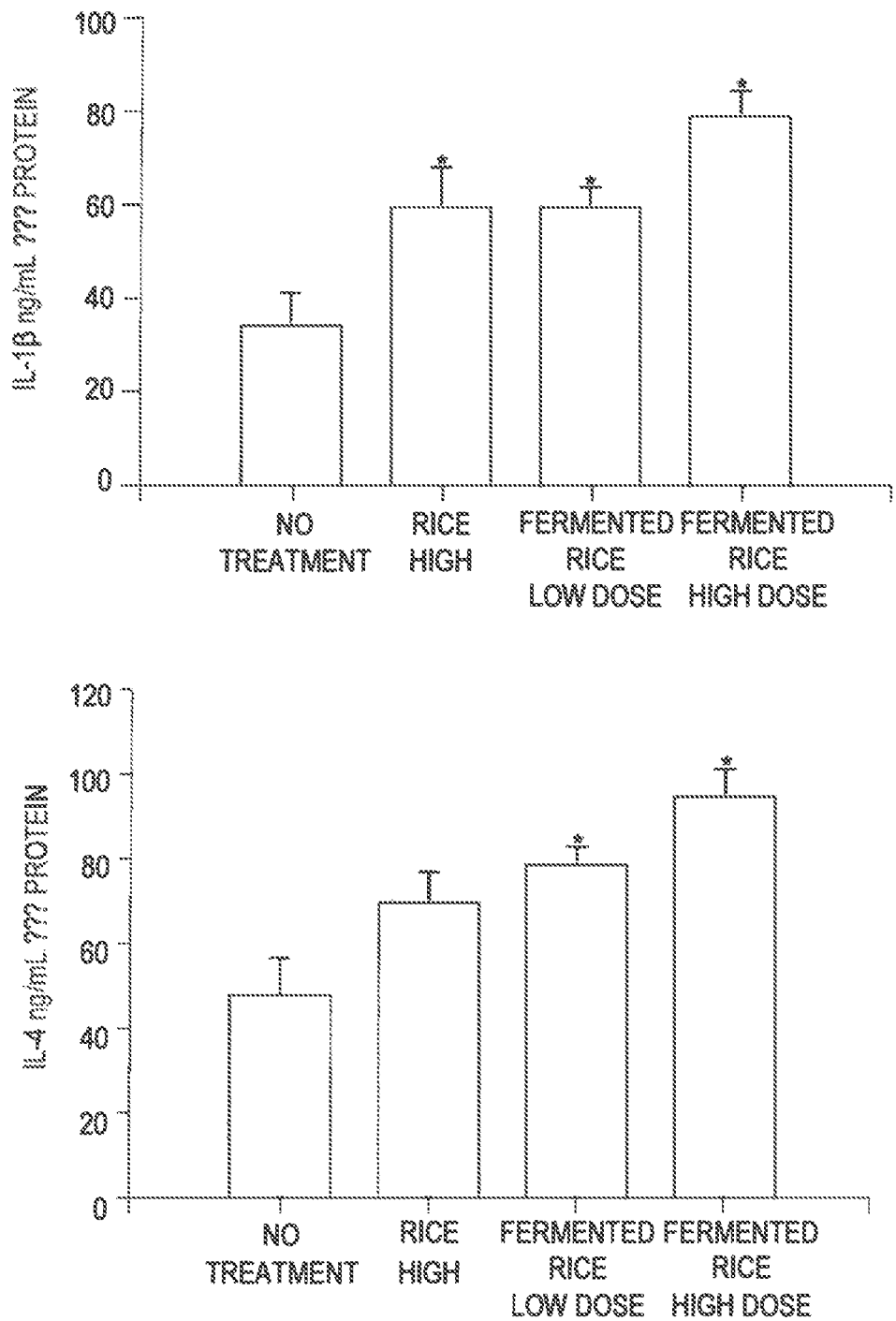
FIG. 22 is a graph depicting IL-1β and IL-4 production in intestinal mucosa of mice supplemented with rice fermented by L. paracasei CBA L74.
Figure 23:
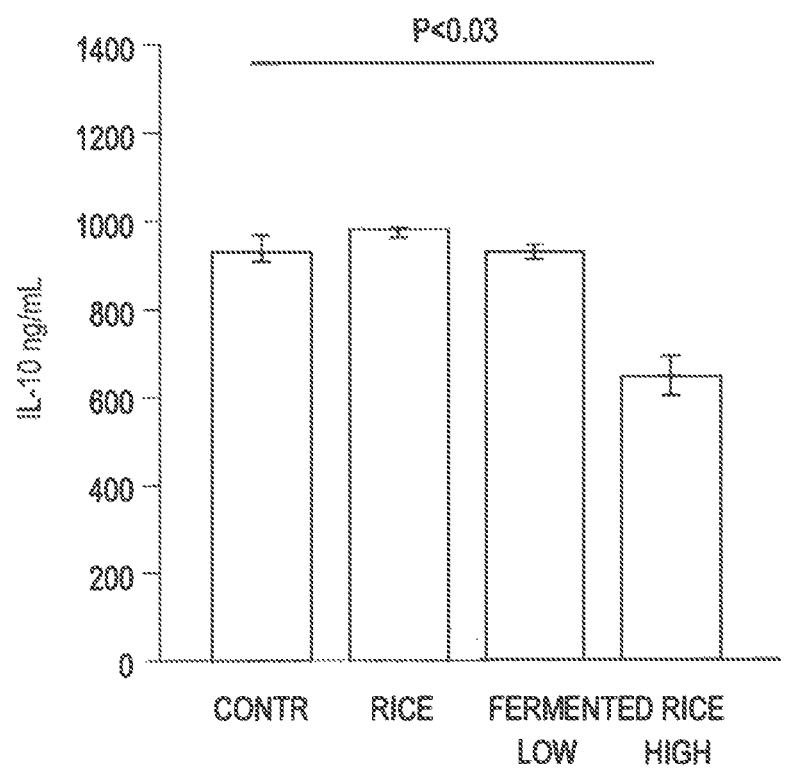
FIG. 23 is a graph depicting IL-10 production in intestinal mucosa of mice supplemented with rice fermented by L. paracasei CBA L74.

We then determined whether administration of *L. paracasei* CBA L74 fermented rice affected the level of anti- and pro-inflammatory cytokines in the intestinal mucosa. As shown in FIG. 22, administration of rice or fermented rice increased both mucosal IL-1β. and IL-4. Supplementation with fermented rice at the highest dose caused a reduction in IL-10 as shown in FIG. 23.

We then determined the effect of different regimen supplementation on mucosal IgA level. Following two weeks of diet supplementation, animals were sacrificed and the intestinal mucosa collected and homogenized. Total IgA was measured by ELISA and values normalized to total mucosal proteins. None of the supplements had significant effects on mucosal IgA.

Figure 24:
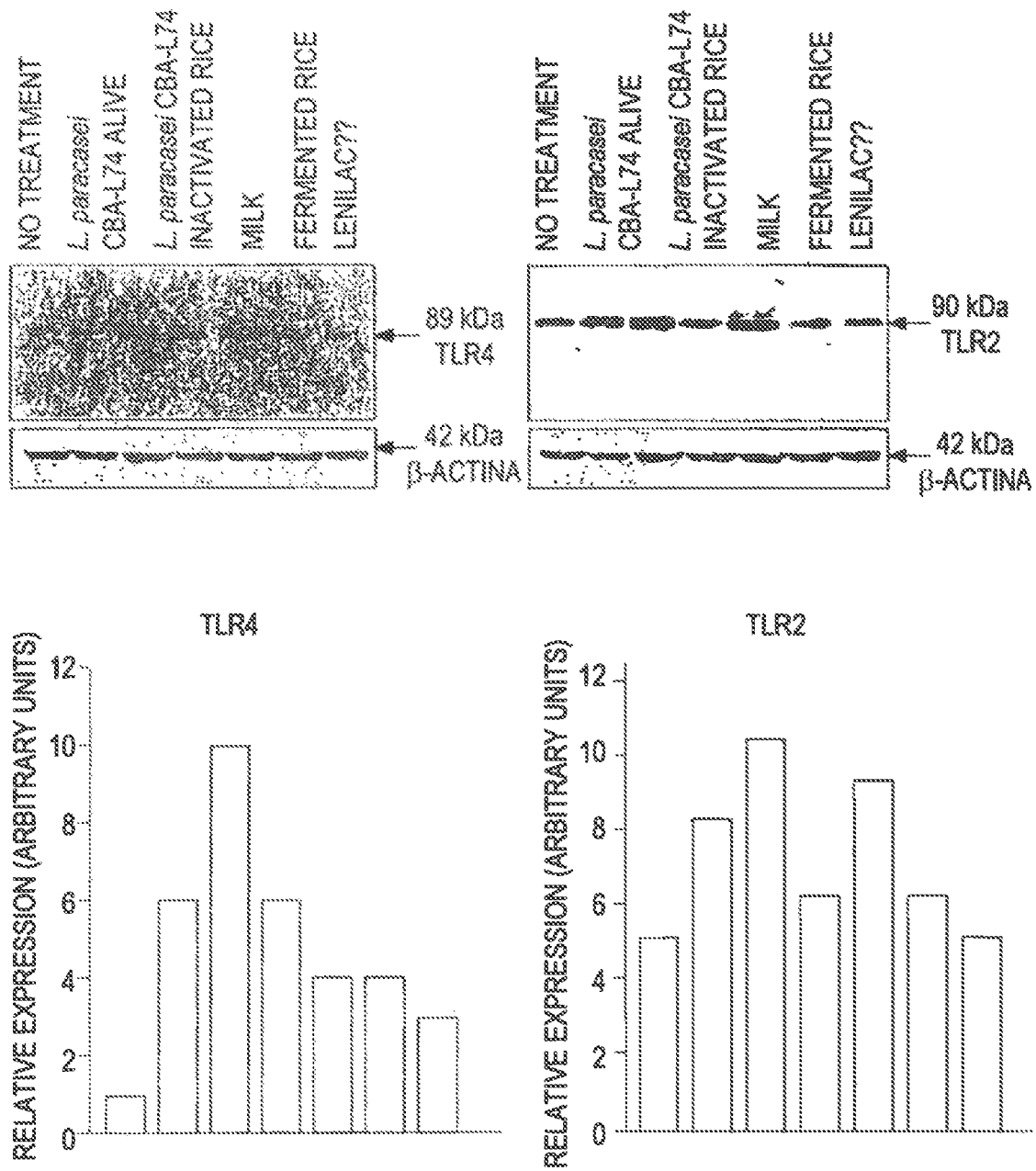
FIG. 24 is an analysis of levels of TLR2 and TLR4 in intestinal mucosa of mice supplemented with rice fermented by L. paracasei CBA L74.
Figure 25A:
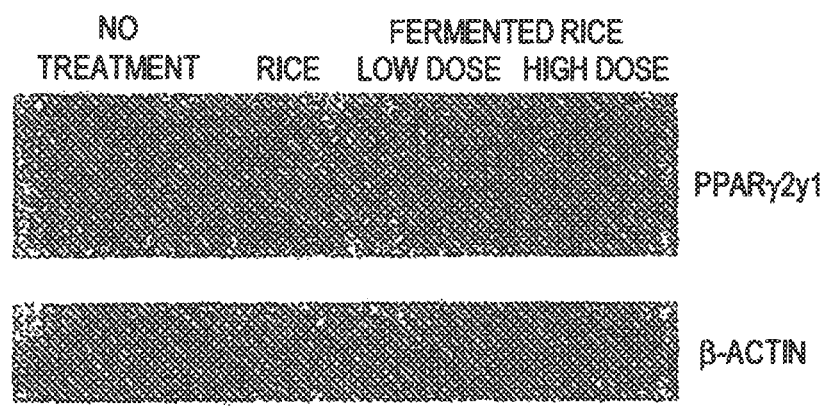
FIG. 25A is an analysis of levels of PPARγ in intestinal mucosa of mice supplemented with rice fermented by L. paracasei CBA L74.
Figure 25B:
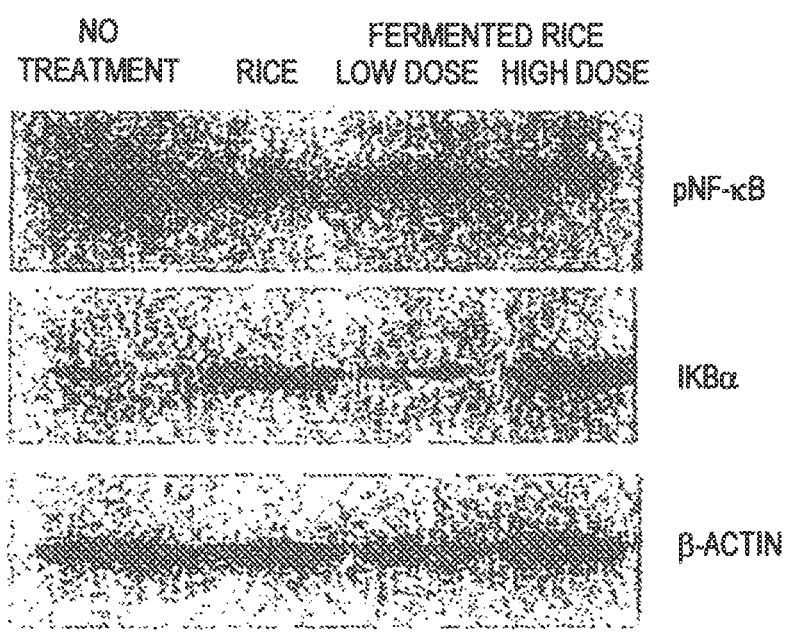
FIG. 25B is an analysis of levels of pNF-kB and IKBα in intestinal mucosa of mice supplemented with rice fermented by *L. paracasei* CBA L74.

We analyzed the effects of rice or *L. paracasei* CBA L74-fermented rice on intestinal mucosa innate immunity. As shown in FIG. 24, diet supplementation with rice and fermented rice (low dose) had only moderate effects on mucosal TLRs. As shown in FIG. 25A, diet supplementation with non-fermented rice drastically increased mucosal PPARγ levels. High doses of fermented rice also increased mucosal PPARγ levels. As shown in FIG. 25B, two weeks of diet supplementation with non-fermented rice reduced NF-κB activation and increased IKB in the mucosa. Supplementation with fermented rice at low doses had no effect compared to control, whereas the higher dose had effects comparable to those observed with non-fermented rice.

We also measured the effects of the dietary administration on anti- and pro-inflammatory cytokines level in the serum. Dietary supplementation with either rice or fermented rice (low dose) had no influence on serum IL-1β and IL-4 levels.

Example 14: Effect of Rice Fermented by *L. paracasei* CBA L74 on Dendritic Cell Phenotype in the Intestinal Mucosa We next focused on the impact of dietary supplementation with nonfermented rice or rice fermented with *L. paracasei* CBA L74 on immune cells relevant to the activity of mucosal-associated immune system, namely dendritic cells and lymphocytes. First we labeled the single cells suspension with anti-CD1 (to identify DC) and with either anti CD-80 and CD-86, MHC-II and CD-40 to determine the level of activity and maturity of intestinal DC in these lymphoid organs. As shown in the table in FIG. 26, we observed a significant effect of fermented rice at high dose on DCs phenotype. Non-fermented rice supplementation (in these experiments we used two different doses) had no effect, whereas the effects of fermented rice on CD80, CD40 and MHC-II level were evident at 100 mg/day and more pronounced at 500 mg/day.

We next determined the ability y of diet supplementation with rice or *L. paracasei* CBA L74 fermented rice to modify the reactivity of DCs to pro-inflammatory stimuli (such as bacterial LPS and CpG). As shown in the table in FIG. 27, exposure of DCs from control mice to LPS or CpG induced an up-regulation of CD80 in control DCs. Supplementation with non-fermented rice did not modify the reactivity to inflammatory stimuli. Supplementation with the tested dose of fermented rice reduced LPS- and CpG-induced CD80 up-regulation.

Example 15: Effect of Rice Fermented by *L. paracasei* CBA L74 on T-Lymphocyte Phenotype in the Intestinal Mucosa We investigated whether dietary supplementation with rice or *L. paracasei* CBA L74 fermented rice was able to influence intestinal T-lymphocyte (either CD4+ and CD8+) polarization toward a Th1 or Th2 phenotype. Peyer's Patches derived lymphocytes were exposed to PHA and then lymphocyte polarization was evaluated by intrakine staining for IL-4 and IFN-γ.

Figure 28:
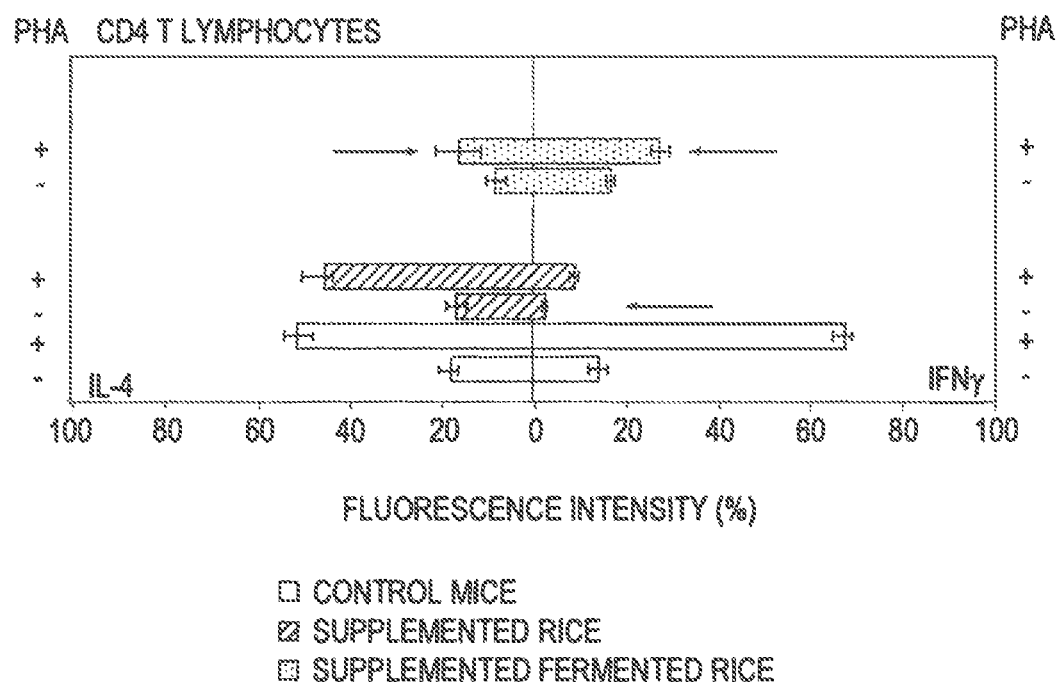
FIG. 28 is a graph depicting intestinal CD4+ lymphocyte phenotypes in mice supplemented with rice fermented by *L. paracasei* CBA L74.
Figure 29:
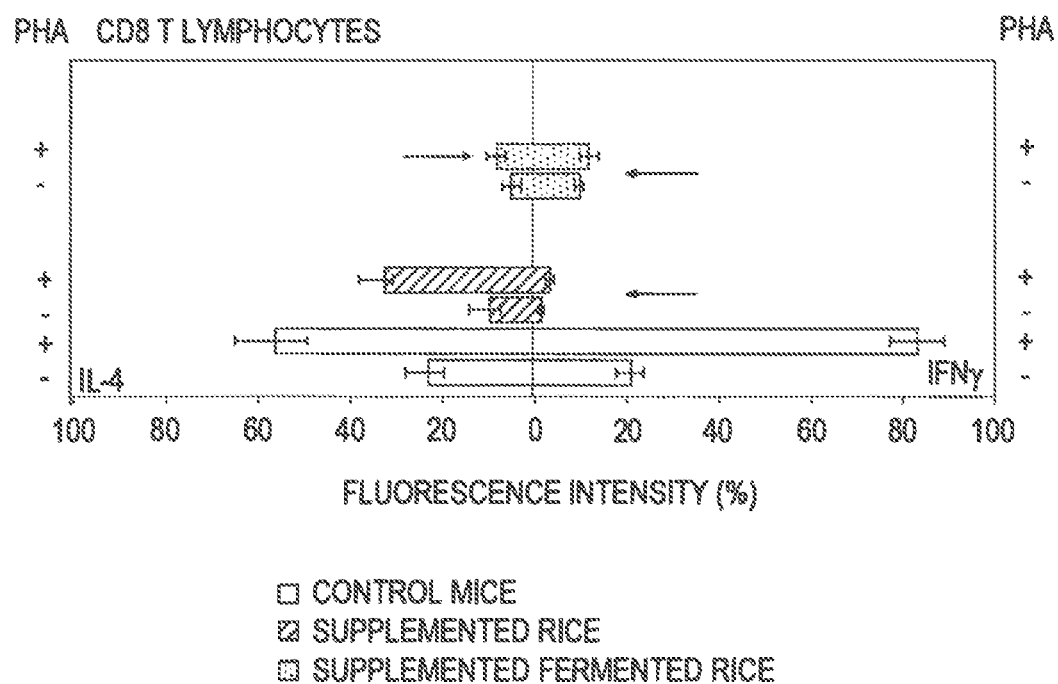
FIG. 29 is a graph depicting intestinal CD8+ lymphocyte phenotypes in mice supplemented with rice fermented by *L. paracasei* CBA L74.

The results of this experiment for CD4+ and CD8+ lymphocytes are shown in FIGS. 28 and 29, respectively. As shown in FIG. 28, in the basal condition, in CD4+ lymphocytes IL-4 and IFNγ were almost in equilibrium since about 10-12% of the cells are positive for these cytokines. As shown in FIG. 29, in CD8+, in the basal condition there was a slight predominance of IL-4 over IFNγ expressing cells. Exposure of either CD4+ or CD8+ lymphocytes to PHA caused a strong increase in intracellular staining for IL-4 and IFNγ, with a predominance of IFNγ production.

In mice receiving non-fermented rice we observed a preponderance of IL-4 production (Th2 phenotype) either in basal condition and following PHA stimulation for both CD4+ and CD8+ lymphocytes. However, IL-4 production was associated to a persistence of IFNγ production in basal condition and, following PHA stimulation we observed an increased expression of this cytokine although the response was blunted as compared to the response in control cells. In mice receiving the fermented rice in basal condition we observed a preponderance of IFNγ positive cells over IL-4, although in basal condition the percentage was comparable (for CD4+) or slightly lower (for CD8+) as compared to controls. Following PHA stimulation, in both cellular populations the cytokine response was blunted as compared to control mice, although directed toward a Th1 phenotype (preponderance of IFNγ positive cells).

Example 16: Effect of *L. paracasei* CBA L74 on IL-10 Production in Monocyte Derived Dendritic Cells (MoDCs) in the Presence of *Salmonella typhimurium*

Figure 30:
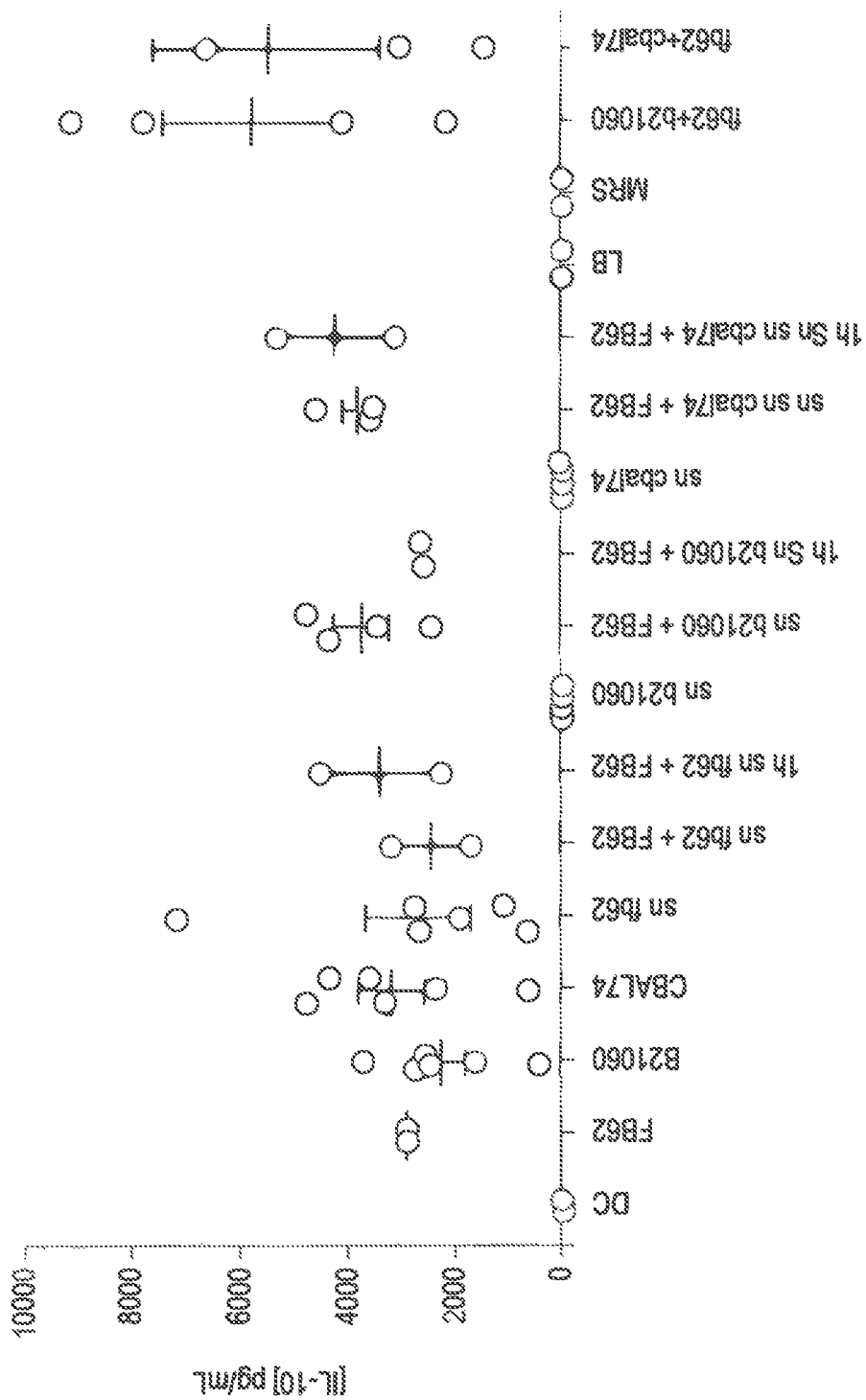
FIG. 30 is a graph depicting an analysis of the effect of *L. paracasei* CBA L74 cells and cell supernatant on IL-10 production in human MoDCs presence of *Salmonella typhimurium*.

We tested the ability of both *L. paracasei* CBA L74 cells and *L. paracasei* CBA L74 cell supernatants to induce production of the anti-inflammatory cytokine, IL-10, in human MoDCs in the presence of the bacterial pathogen, *Salmonella typhimurium*. Human MoDCs were obtained from at least four, and in some cases, seven donors. As shown in FIG. 30, *Salmonella typhimurium* ("FB62"), the control *Lactobacillus* strain, *L. paracasei* 21060 ("B21060") and *L. paracasei* CBA L74 ("CBAL74") cells all induced IL-10 production. In contrast, although supernatant from *Salmonella typhimurium* ("sn fb62") induced IL-10 production, supernatants from both Lactobacilli, *Lactobacillus* strain, *L. paracasei* 21060 ("sn b21060") and *L. paracasei* CBA L74 ("sn cba174") did not. Co-incubation of *L. paracasei* CBA L74 supernatant with *Salmonella typhimurium* ("sn cba174+FB62") induced IL-10 to levels over and above that seen with *Salmonella typhimurium* alone ("sn fb62+FB62"). Interestingly, a similar effect was observed even if the MoDCs were preconditioned with *L. paracasei* CBA L74 supernatant for only one hour and then washed to remove the supernatant ("1 h sn cba174+FB62").

Example 17: Effect of *L. paracasei* CBA L74 on IL-12p70 Production in Monocyte Derived Dendritic Cells (MoDCs) in the Presence of *Salmonella typhimurium*

Figure 31:
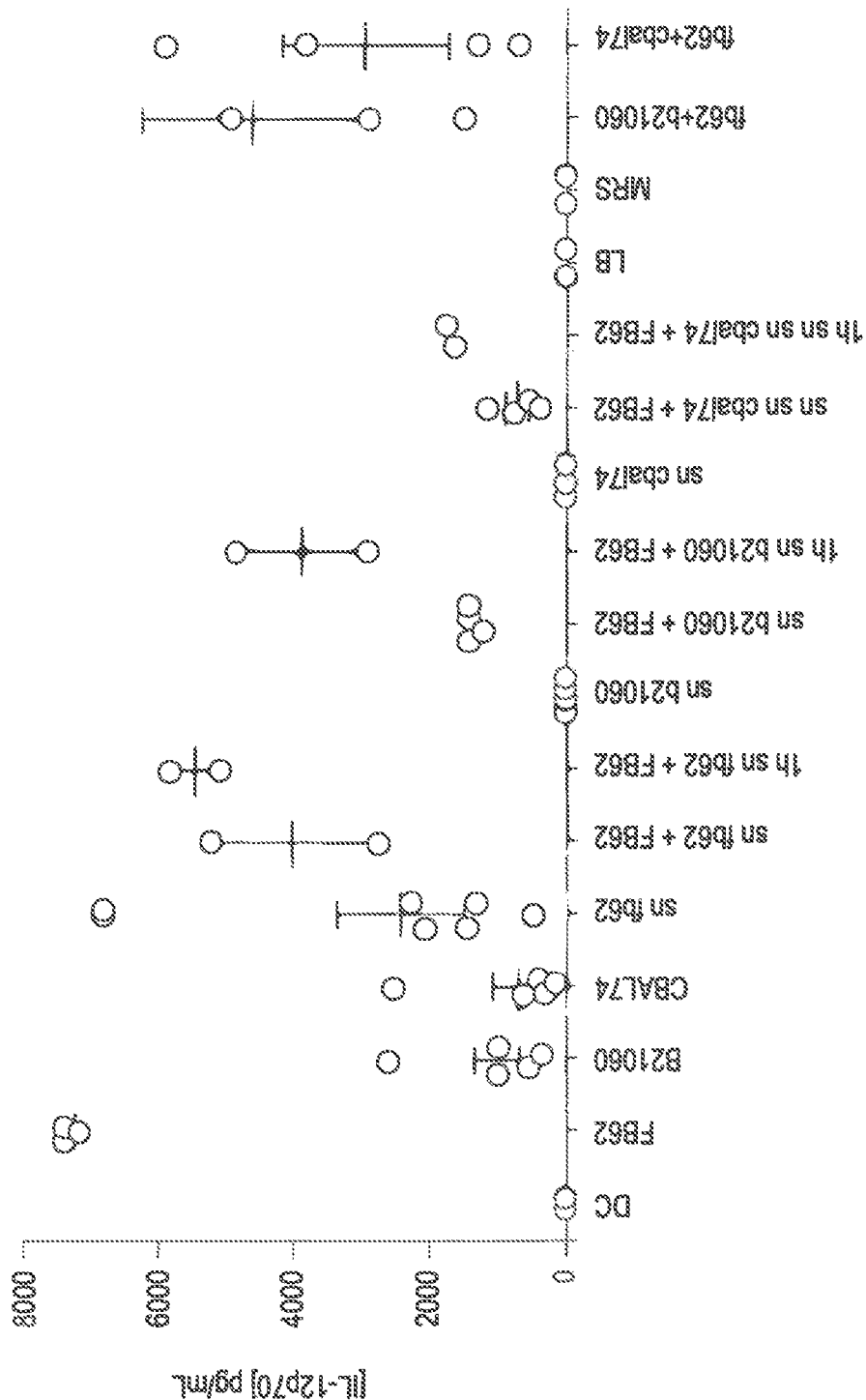
FIG. 31 is a graph depicting an analysis of the effect of *L. paracasei* CBA L74 cells and cell supernatant on IL-12p70 production in human MoDCs in the presence of *Salmonella typhimurium*.

We tested the ability of both *L. paracasei* CBA L74 cells and *L. paracasei* CBA L74 cell supernatants to induce production of the pro-inflammatory cytokine, IL-12p70, in human MoDCs in the presence of the bacterial pathogen, *Salmonella typhimurium*. Human MoDCs were obtained from at least four, and in some cases, seven donors. The results of this experiment are shown in FIG. 31. In contrast to the results obtained in Example 16 for the anti-inflammatory cytokine, we found that *Salmonella typhimurium* ("FB62") induced high levels of IL-12p70 while the control *Lactobacillus* strain, *L. paracasei* 21060 ("B21060") and *L. paracasei* CBA L74 ("CBAL74") cells induced only low levels of IL-12p70. Here again, supernatant from *Salmonella typhimurium* ("sn fb62") induced IL-12p70 production, but supernatants from both *Lactobacillus* strains, *L. paracasei* 21060 ("sn b21060") and *L. paracasei* CBA L74 ("sn cba174") did not. Co-incubation of *L. paracasei* CBA L74 supernatant with *Salmonella typhimurium* ("sn cba174+FB62") caused a striking reduction in IL-12p70 production. The effect was observed even if the MoDCs were preconditioned with *L. paracasei* CBA L74 supernatant for only one hour and then washed to remove the supernatant ("1 h sn cba174+FB62"). This reduction exceeded that observed for the control *Lactobacillus*, *L. paracasei* 21060 ("1 h sn b21060+FB62"). These data suggest that both *L. paracasei* CBA L74 and culture supernatant from *L. paracasei* CBA L74 have anti-inflammatory properties that can mitigate the inflammation induced by the bacterial pathogen, *Salmonella typhimurium*.

Example 18: Effect of *L. paracasei* CBA L74 Fermented Milk on IL-10 Production in Monocyte-Derived Dendritic Cells (MoDCs) in the Presence of *Salmonella typhimurium*

Figure 32:
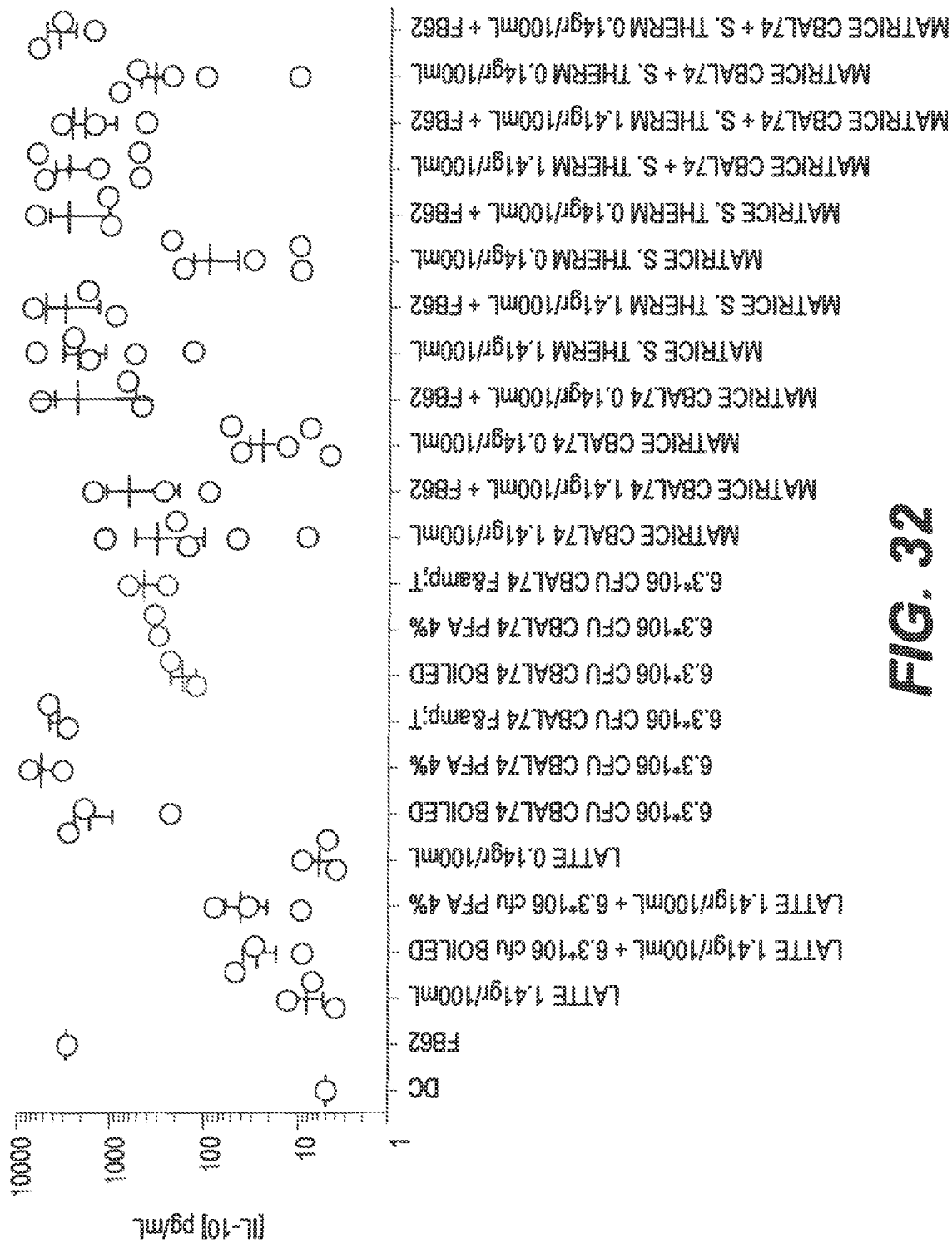
FIG. 32 is a graph depicting an analysis of the effect of *L. paracasei* CBA L74 fermented milk on IL-10 production in human MoDCs presence of *Salmonella typhimurium* and the effect of inactivation of *L. paracasei* CBA L74 on IL-10 production in human MoDCs in the presence of *Salmonella typhimurium*.

We tested the ability of *L. paracasei* CBA L74-fermented milk to induce production of the anti-inflammatory cytokine, IL-10, in human MoDCs in the presence of the bacterial pathogen, *Salmonella typhimurium*. The results of this experiment are shown in FIG. 32. Although unactivated MoDCs do not usually produce IL-10, we found that incubation of MoDCs with *L. paracasei* CBA L74-fermented milk induced dose-dependent IL-10 production (see "matrice CBAL74 1.41 gr/100 ml" and "matrice CBAL74 0.14 gr/100 ml"). The capacity was retained even in the presence of *Salmonella typhimurium* (see "matrice CBAL74 1.41 gr/100 ml+FB62" and "matrice CBAL74 0.14 gr/100 ml+FB62").

FIG. 32 also shows that *L. paracasei* CBA L74 that had been activated by heat ("6.3*106 CFU CBA74 boiled"), paraformaldehyde treatment ("6.3*106 CFU CBA74 PFA") or freeze-thawing ("6.3*106 CFU CBA74 F&T") retained the ability to induce IL-10.

Figure 33:
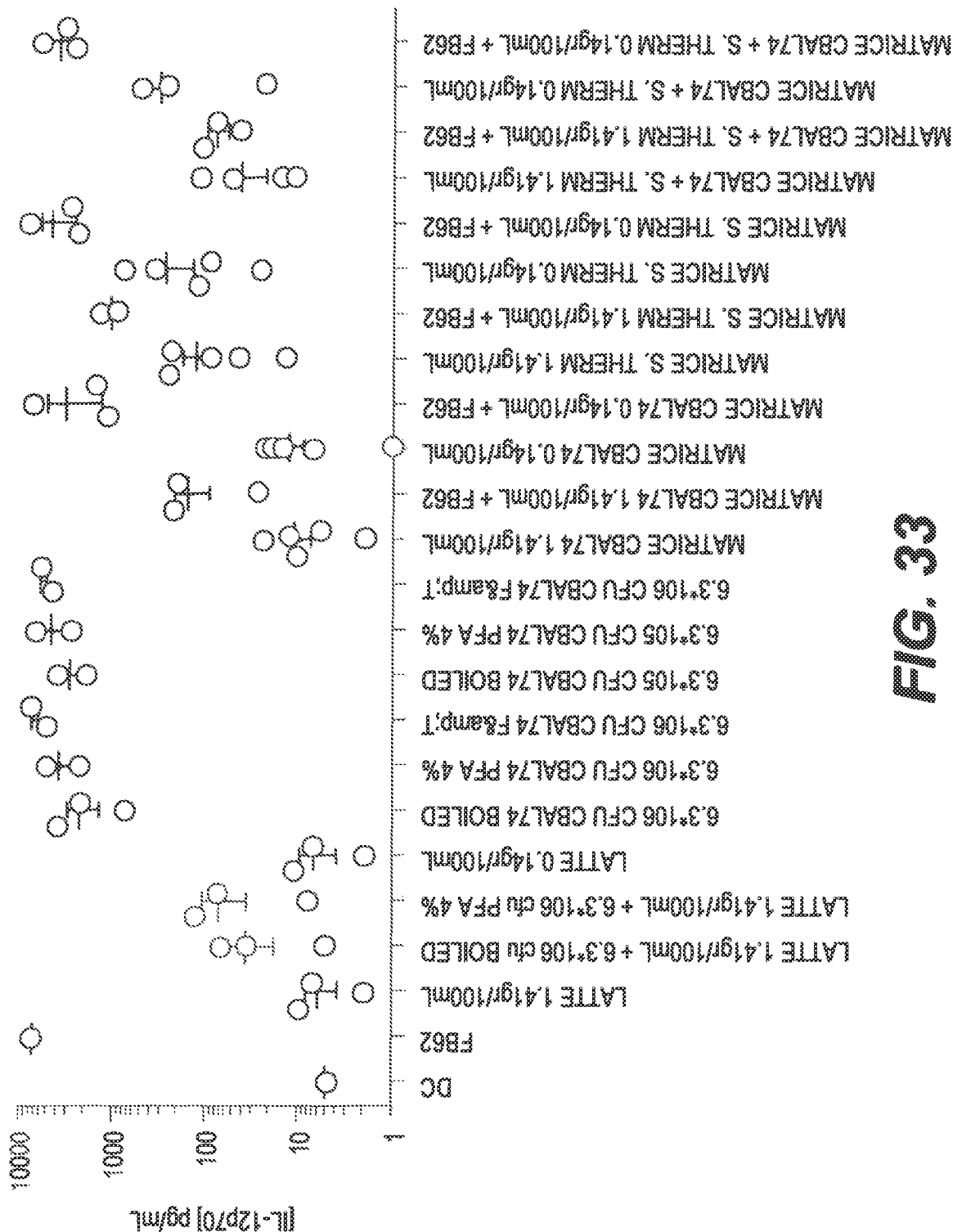
FIG. 33 is a graph depicting an analysis of the effect of *L. paracasei* CBA L74 fermented milk on IL-12p70 production in human MoDCs presence of *Salmonella typhimurium* and the effect of inactivation of *L. paracasei* CBA L74 on I L-12p70 production in human MoDCs in the presence of *Salmonella typhimurium*.

As we observed for *L. paracasei* CBA L74 culture media, *L. paracasei* CBA L74-fermented milk caused a significant, dose-dependent reduction in production of IL-12p70 induced by *Salmonella typhimurium*. (FIG. 33). *S. thermophilus* fermented milk caused an increase in IL-12p70 production in the presence of *Salmonella typhimurium*. However, milk fermented by *L. paracasei* CBA L74 did not stimulate IL-12p70 production, consistent with the anti-inflammatory properties of *L. paracasei* CBA L74. These data suggest that *L. paracasei* CBA L74 retained its anti-inflammatory properties even in the presence of more pro-inflammatory species.

Example 19: Effect of *L. paracasei* CBA L74 Cell Supernatants on IL-10 and IL 12p70 Production in Monocyte-Derived Dendritic Cells (MoDCs) in the Presence of *Enterobacter sakazaki*

We tested the ability of *L. paracasei* CBA L74 cell supernatants to induce production of the anti-inflammatory cytokine, IL-10 and the pro-inflammatory cytokine, IL-12p70, in human MoDCs in the presence of the bacterial pathogen, *Enterobacter* sakazaki. We tested two strains of *E. sakazaki*, N9 and N13. *E. sakazaki* induced the production of both IL-10 and IL-12p70 in human MoDCs. The addition of *L. paracasei* CBA L74 cell supernatants resulted in an increase in IL-10 and a significant decrease in IL-12p70.

Example 20: Effect of *L. paracasei* CBA L74 Fermented Rice on Cytokine Production in a Tissue Explant Model in the Presence of *Salmonella typhimurium*

Figure 34:
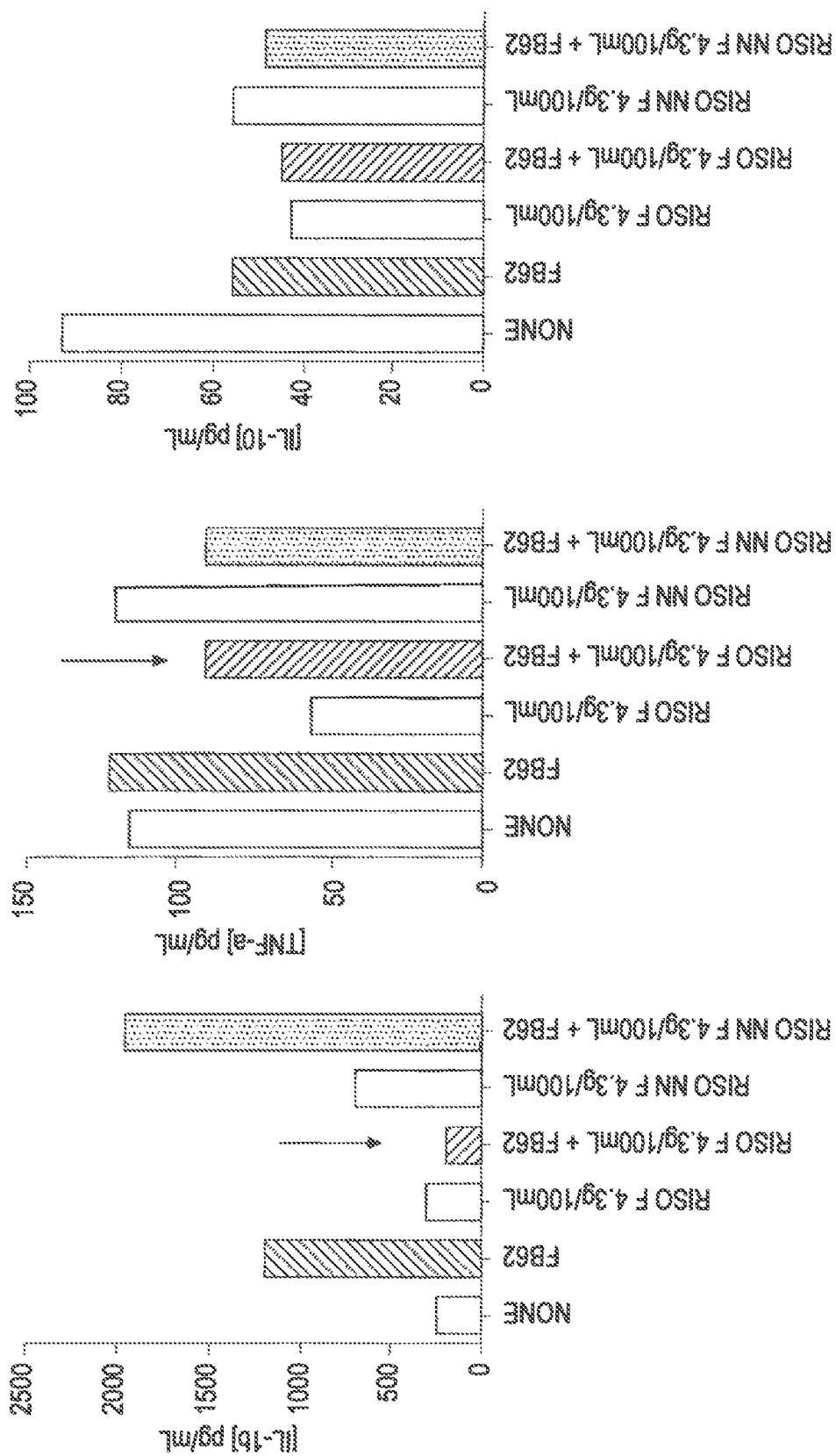
FIG. 34 is a graph depicting an analysis of the effect of *L. paracasei* CBA L74 fermented rice on IL-1β, TNF-α and IL-10 in a gut tissue explant model in the presence of *Salmonella typhimurium*.

Mouse gut epithelium as used to set up three-dimensional co-culture system as described in Abud (Exp. Cell Res. 303: 252-262 (2005)). Tissue explants were cultured for 24 hour in the presence of 100% 02 with a pressure of one atmosphere. The lower chamber contained 1 ml of hEC DMEM plus ITS-X and EGF. The upper chamber contained 200 ml of medium plus either *S. typhimurium, L. paracasei* CBA L74 fermented rice, or a combination of *S. typhimurium* and *L. paracasei* CBA L74 fermented rice. Supernatants were harvested and levels of IL-1β, TNF-α, and IL-10 were assayed by ELISA. As shown in FIG. 34, the addition of fermented rice significantly reduced production of the pro-inflammatory cytokines, IL-1β and TNF-α in the presence of *S. typhimurium*, with only a moderate effect on the levels of the antiinflammatory cytokine, IL-10.

It is to be understood that the present invention is by no means limited only to the particular constructions herein disclosed and shown in the drawings, but also comprises any modifications or equivalents within the scope of the claims.

What is claimed is:

1. A method of treating a subject having a gastrointestinal disorder, the method comprising:
    a) identifying a subject having a gastrointestinal disorder;
    b) administering to the subject an effective amount of a pharmaceutical composition comprising probiotic bacterium, *Lactobacillus paracasei* CBA L74, International Depository Accession Number LMG P-24778, wherein the *Lactobacillus paracasei* CBA L74 cells present in the composition are dead or have been rendered incapable of cell division.

2. The method of claim 1, wherein the gastrointestinal disorder is a mucosal immune system deficit, a food allergy, a disorder associated with diarrhea, a bacterial or viral infection, irritable bowel syndrome, inflammatory bowel disease, Crohn's disease, celiac disease or necrotizing enterocolitis.

3. The method of claim 2, wherein the mucosal immune system deficit is an immature immune system.

4. The method of claim 1, wherein the subject is a human infant.

5. A method of treating a subject having a gastrointestinal disorder, the method comprising:
    administering to the subject an effective amount of a pharmaceutical composition comprising a culture supernatant of probiotic bacterium, *Lactobacillus paracasei* CBA L74, Intranational Depository Accession Number LMG P-24778, wherein any *Lactobacillus paracasei* CBA L74 cells present in the composition are dead or have been rendered incapable of cell division.

6. The method of claim 5, wherein the gastrointestinal disorder is a mucosal immune system deficit, a food allergy, a disorder associated with diarrhea, a bacterial or viral infection, irritable bowel syndrome, inflammatory bowel disease, Crohn's disease, celiac disease or necrotizing enterocolitis.

7. The method of claim 6, wherein the mucosal immune system deficit is an immature immune system.

8. The method of claim 5, wherein the subject is a human infant.

9. The method of claim 5, wherein the composition is substantially free of intact *Lactobacillus paracasei* CBA L74 cells.

10. The method of claim 1, wherein the probiotic bacterium is in a unit dosage form of about $1 \times 10^2$ cfu/g to about $1 \times 10^{12}$ cfu/g dry weight.

11. The method of claim 5, wherein the composition comprises 0.01 to 1,000 mg per kg of the culture supernatant based on the weight of the subject.

* * * * *